US009115352B2

(12) United States Patent
Van den Brulle et al.

(10) Patent No.: US 9,115,352 B2
(45) Date of Patent: Aug. 25, 2015

(54) METHOD FOR THE PREPARATION OF A NUCLEIC ACID LIBRARY

(75) Inventors: Jan Van den Brulle, Munich (DE); Markus Fuhrmann, Maxhutta-Haidhof (DE); Ralf Strohner, Munich (DE)

(73) Assignee: Sloning BioTechnology GmbH, Martinsried (DE)

( * ) Notice: Subject to any disclaimer, the term of this patent is extended or adjusted under 35 U.S.C. 154(b) by 616 days.

(21) Appl. No.: 12/414,174

(22) Filed: Mar. 30, 2009

(65) Prior Publication Data

US 2010/0022410 A1    Jan. 28, 2010

(30) Foreign Application Priority Data

Mar. 31, 2008    (EP) .................................... 08006472

(51) Int. Cl.
*C12N 15/10*    (2006.01)
*C12N 15/66*    (2006.01)

(52) U.S. Cl.
CPC ............ *C12N 15/10* (2013.01); *C12N 15/1093* (2013.01); *C12N 15/66* (2013.01); *C12N 15/1068* (2013.01)

(58) Field of Classification Search
CPC .................................................. C12N 15/1093
See application file for complete search history.

(56) References Cited

U.S. PATENT DOCUMENTS

| | | | |
|---|---|---|---|
| 4,652,639 A | 3/1987 | Stabinsky | |
| 5,093,251 A | 3/1992 | Richards et al. | |
| 5,132,215 A | 7/1992 | Jayaraman et al. | |
| 5,397,698 A | 3/1995 | Goodman et al. | |
| 5,508,169 A | 4/1996 | Deugan et al. | |
| 5,710,000 A | 1/1998 | Sapolsky et al. | |
| 5,770,365 A | 6/1998 | Lane et al. | |
| 5,770,380 A * | 6/1998 | Hamilton et al. | 435/7.1 |
| 5,858,686 A | 1/1999 | Schlessinger et al. | |
| 5,888,737 A | 3/1999 | DuBridge et al. | |
| 5,981,190 A | 11/1999 | Israel | |
| 6,110,668 A | 8/2000 | Strizhov et al. | |
| 6,472,184 B1 | 10/2002 | Hegemann | |
| 6,485,944 B1 | 11/2002 | Church et al. | |
| 2002/0048772 A1* | 4/2002 | Dahiyat et al. | 435/7.1 |
| 2003/0215837 A1* | 11/2003 | Frey et al. | 435/6 |
| 2006/0115850 A1 | 6/2006 | Schatz | |
| 2006/0194202 A1* | 8/2006 | Schatz et al. | 435/6 |
| 2008/0044862 A1 | 2/2008 | Schatz et al. | |

FOREIGN PATENT DOCUMENTS

| | | |
|---|---|---|
| EP | 0245130 | 11/1987 |
| EP | 0533838 | 3/1993 |
| EP | 1411122 | 4/2004 |
| WO | WO98/10095 | 3/1992 |
| WO | WO93/19202 | 9/1993 |
| WO | WO95/17413 | 6/1995 |
| WO | WO96/12014 | 4/1996 |
| WO | 98/15567 | 4/1998 |
| WO | 99/47536 | 9/1999 |
| WO | WO99/47536 | 9/1999 |
| WO | 00/75368 | 12/2000 |
| WO | WO01/61036 | 8/2001 |
| WO | WO01/75180 | 10/2001 |
| WO | 02010449 | 7/2002 |
| WO | 2004035781 | 4/2004 |

OTHER PUBLICATIONS

Waldmann et al. Slonomics: An Advanced Technology for Automated Gene Synthesis; Innovations in Pharmaceutical Technology; 2006; pp. 59, 60, 62, and 64.*
Werner Besenmatter, Ph.D. Thesis, Diss. ETH No. 16912, ETH Zurich, 2007, "Protein Engineering with Genetic Selection: Tolerance of Enzyme Activity to Sequence Change".
Innovative Science for Successful Business, 3rd Partnering Day for Biomedical Research, Oct. 19, 2006, Abstract book (pp. 1, 3, 4, 107 and 108), pp. 1-5.
Innovative Science for Successful Business, 3rd Partnering Day for Biomedical Research, Oct. 19, 2006, Archive.
Crawford, M., et al., Briefings in Functional Genomics and Proteomics, vol. 2, No. 1, pp. 72-79, Apr. 2003.
Hoare, D.G., et al., J. Biol. Chem. 242, pp. 2447-2453 (1967).
Xiong et al: "Non-polymerase-cycling-assembly-based chemical gene synthesis: Strategies, methods, and progress", Biotechnology Advances, Elsevier Publishing, Barking, GB, vol. 26, No. 2, Nov. 7, 2007, pp. 121-134, XP022426820.
Eugen Uhlmann: "An alternative approach in gene synthesis: use of long selfpriming oligodeoxynucleotides for the construction of double-stranded DNA", Gene, vol. 71, Nov. 15, 1988, pp. 29-40, XP000941756.
Wlodek Mandecki et al.: "A totally synthetic plasmid for general cloning, gene expression and mutagenesis in *Escherichia coli*", Gene, vol. 94, Sep. 28, 1990, pp. 103-107, XP000941757.
Van den Brulle, et al.: "A novel solid phase technology for high-throughput gene synthesis", Biotechniques vol. 45, No. 3, 2008, pp. 340-343.
Padgett KA et al: I"Creating seamless junctions independent of restriction site in PCR cloning", Gene, Elsevier Biomedical Press. Amsterdam, NL, vol . 168, No. 1, Feb. 2, 1996, pp. 31-35, XP004042930.
Kato K: "Description of the Entire MRNA Population by A3' End CDNA Fragment Generated by Class IIS Restriction Enzymes", Nucleic Acids Research, Oxford University, Press, Surrey, GB, vol. 23, No. 18, Sep. 1, 1995, pp. 3685-3690, XP002008304.
Shibata Y et al: Cloning full-length, Cap-Trapper-selected cDNAs by using the single-strand linker ligation method. II, Biotechniques, vol. 30, No. 6, Jun. 2001 , pp. 1250-1254, XP002197302.
Unrau Paul et al: "Non-cloning amplification of specific DNA fragments from whole genomic DNA digests using DNA, indexers'", Gene, Elsevier Biomedical Press. Amsterdam, NL, vol. 145, No. 2, 1994, pp. 163-169, XP002149819.

(Continued)

*Primary Examiner* — Karlheinz R Skowronek
*Assistant Examiner* — Lianko Garyu
(74) *Attorney, Agent, or Firm* — Paul F. Wiegel

(57) ABSTRACT

The present invention is related to a method for preparing a nucleic acid library comprising a plurality of various elements or nucleic acid molecules that differ in a controlled manner at one or several distinct nucleotide positions.

21 Claims, 12 Drawing Sheets

(56) References Cited

OTHER PUBLICATIONS

Velculescu Ve et al: "Serial Analysis of Gene Expression" Science, American Association for the Advancement of Science US, vol. 270, No. 5235, Oct. 20, 1995, pp. 484-487, XP001024449.

Shao-Chi Huang et al., "Binding of biotinylated DNA to Streptavidin-Coated Polystryrene Latex." 222 Analytical Biochemistry (1994) 441-449.

Bolli, et al.; Pyranosyl-RNA:chiroselective self-assembly of base sequences by ligative oligomerization oftetranucleotide-2',3'-cyclophosphates, 1997, Chem.Biol. 4(4): 309-320.

Hoare & Koshland; A method for the quantitative modification and estimation of carboxylic acid groups in proteins, 1967, 1. Biol. Chem. 242(10): 2447-2453.

Sekiya, et al.; Total Synthesis of a tyrosine suppressor tRNA gene. xv. Synthesis of the promoter region, 1979, J. Bioi. Chem. 254(13): 5781-5786.

Sekiya, et al.; Total synthesis of a tyrosine suppressor transfer RNA gene. XVI Enzymatic joinings to form the total 207-base pair-long DNA, 1979, 1. Biol. Chem. 254(13): 5787-5801.

Roberts, R.J., and D. Macelis (1999) REBASE-restriction enzymes and methylases. Nucleic Acids Res 27: 312-3.

Berlin, (1999), Current Issues Molec. Biol., 'DNA Splicing by Directed Ligation (SDL)', 1(1), 21-30.

Werner Besenmatter, Ph.D. Thesis, Diss. ETH No. 16912, ETH Zurich, 2007, "Protein Engineering with Genetic Selection: Tolerance of Enzyme Activity to Sequence Change" pp. 6, 36 and 62.

Innovative Science for Successful Business, 3rd Partnering Day for Biomedical Research, Oct. 19, 2006, Abstract book (pp. 1, 3, 4, 107 and 108).

Innovative Science for Successful Business, 3rd Partnering Day for Biomedical Research, Oct. 19, 2006, Archive pp. 1-5.

Sloning Biotechnology, Oct. 19, 2006, Presentation: 'Turning Information into Molecules'.

Sloning Biotechnology, Oct. 19, 2006, Poster: "The SlonomicsTM Gene Synthesis Technology".

Sloning Biotechnology, Oct. 19, 2006, Poster: "Production of High Quality Mutant Libraries Using an Automated Gene Synthesis Technology".

\* cited by examiner

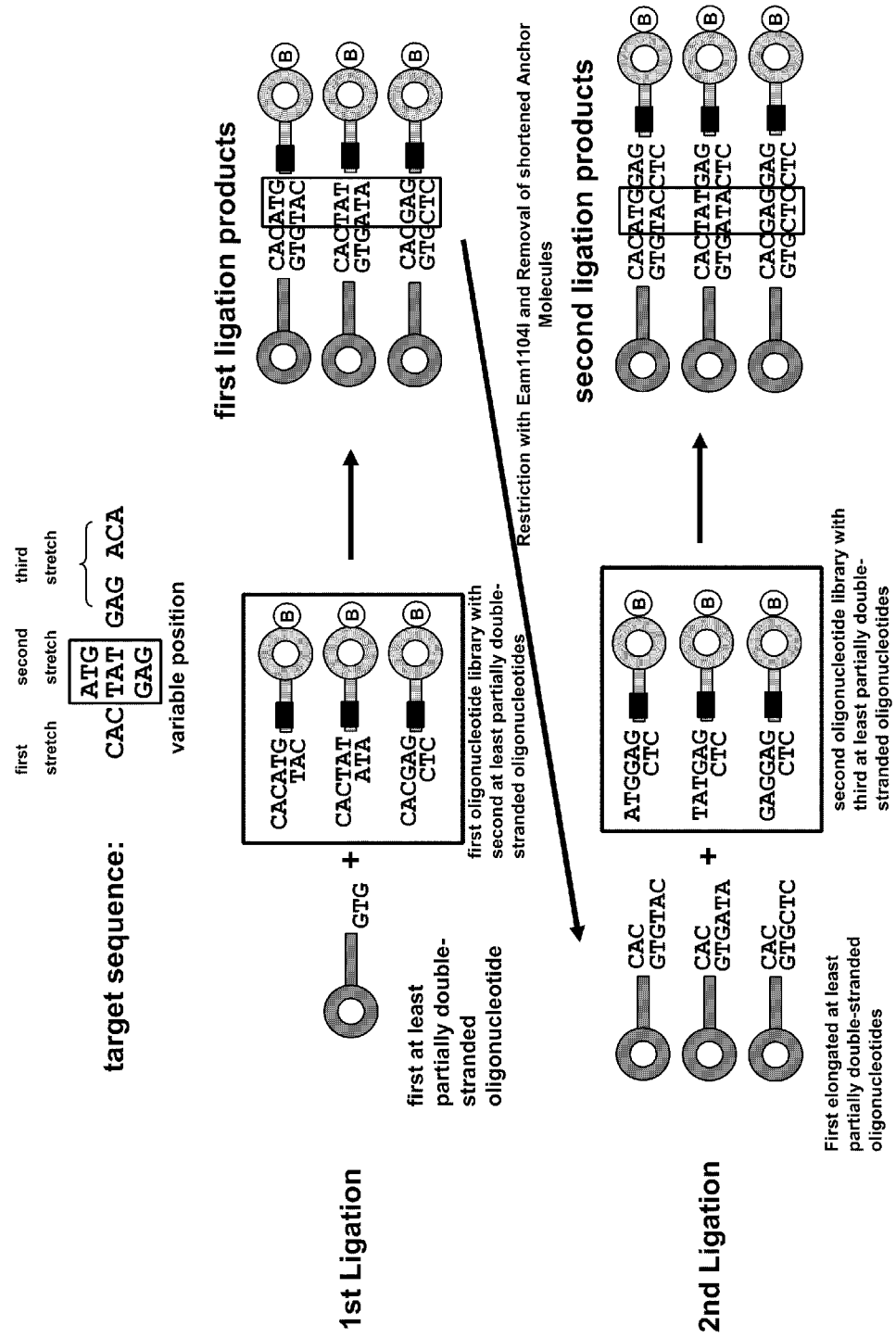

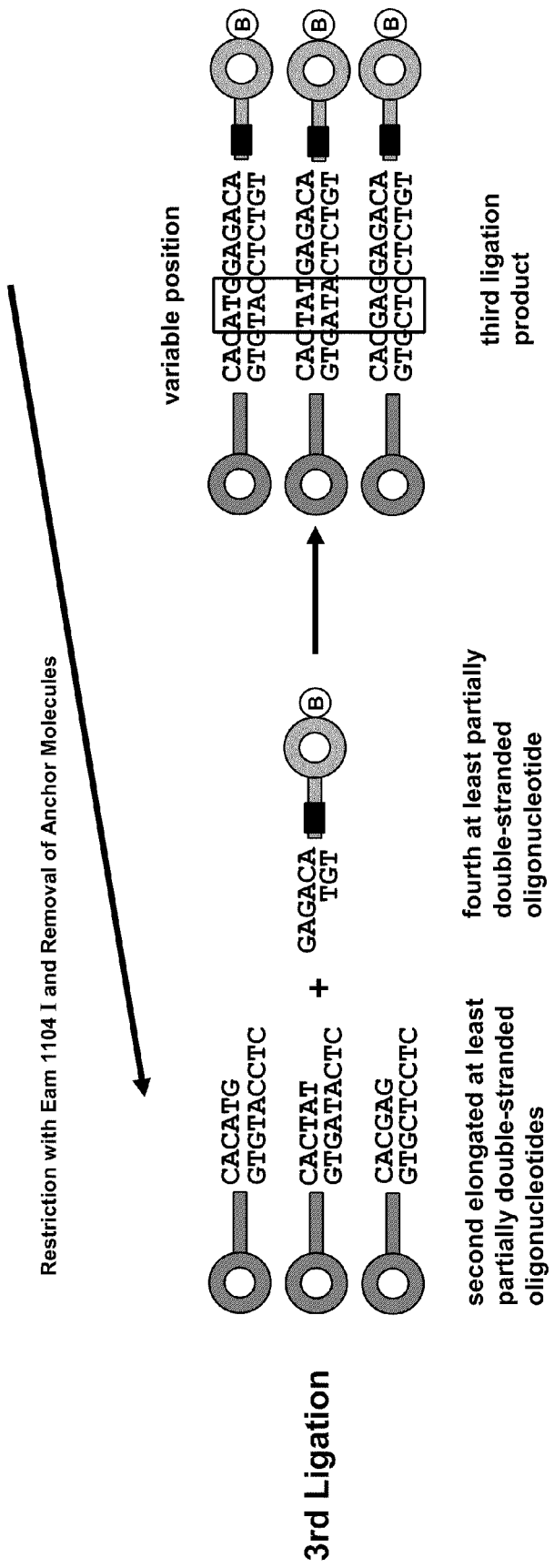
Fig. 1 (2)

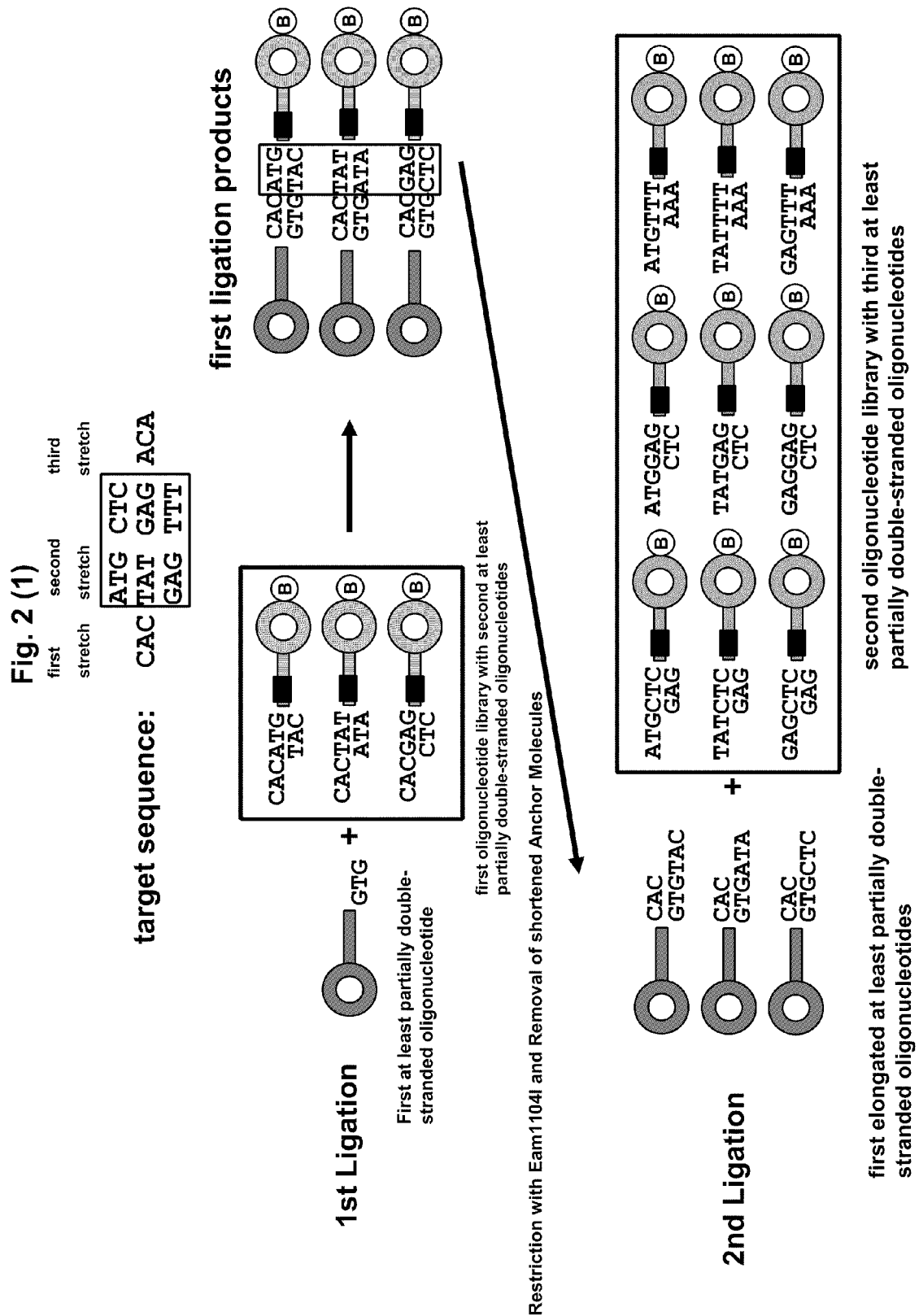

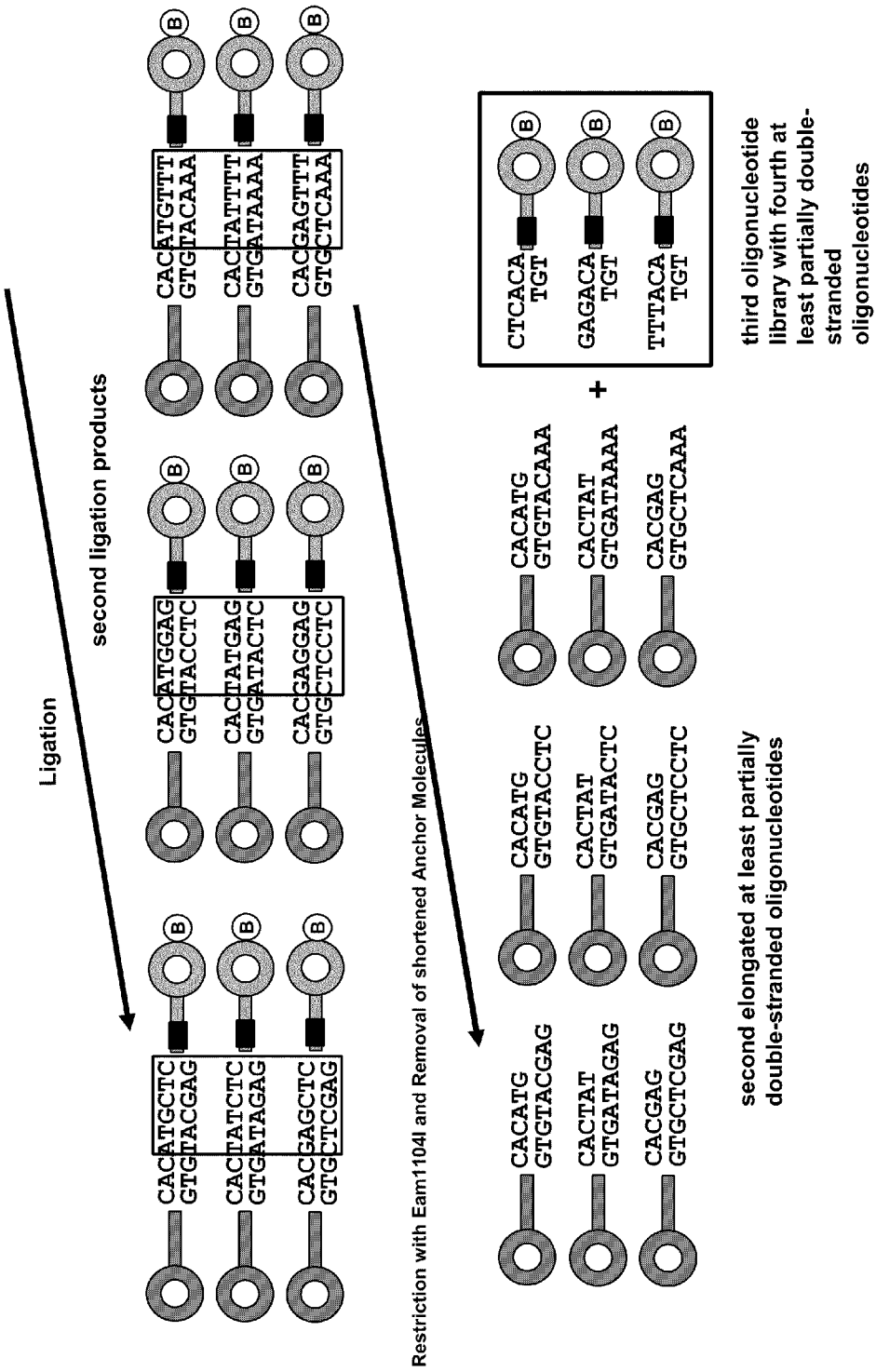
Fig. 2 (2)

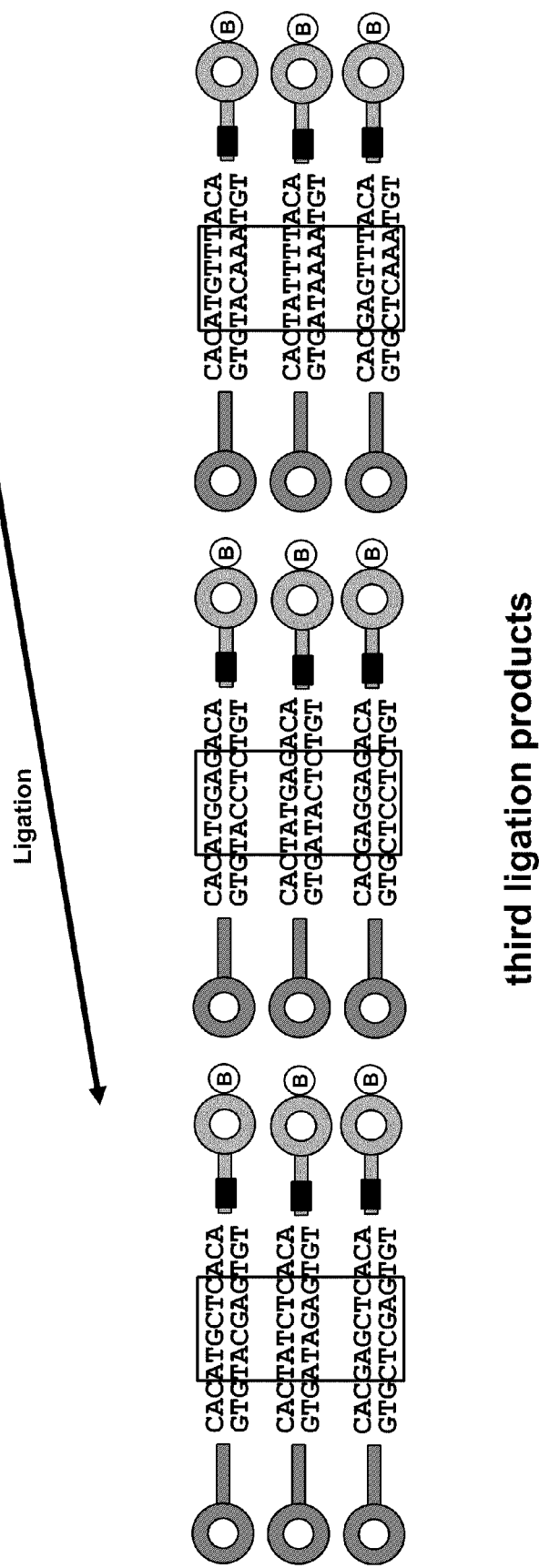
Fig. 2 (3)

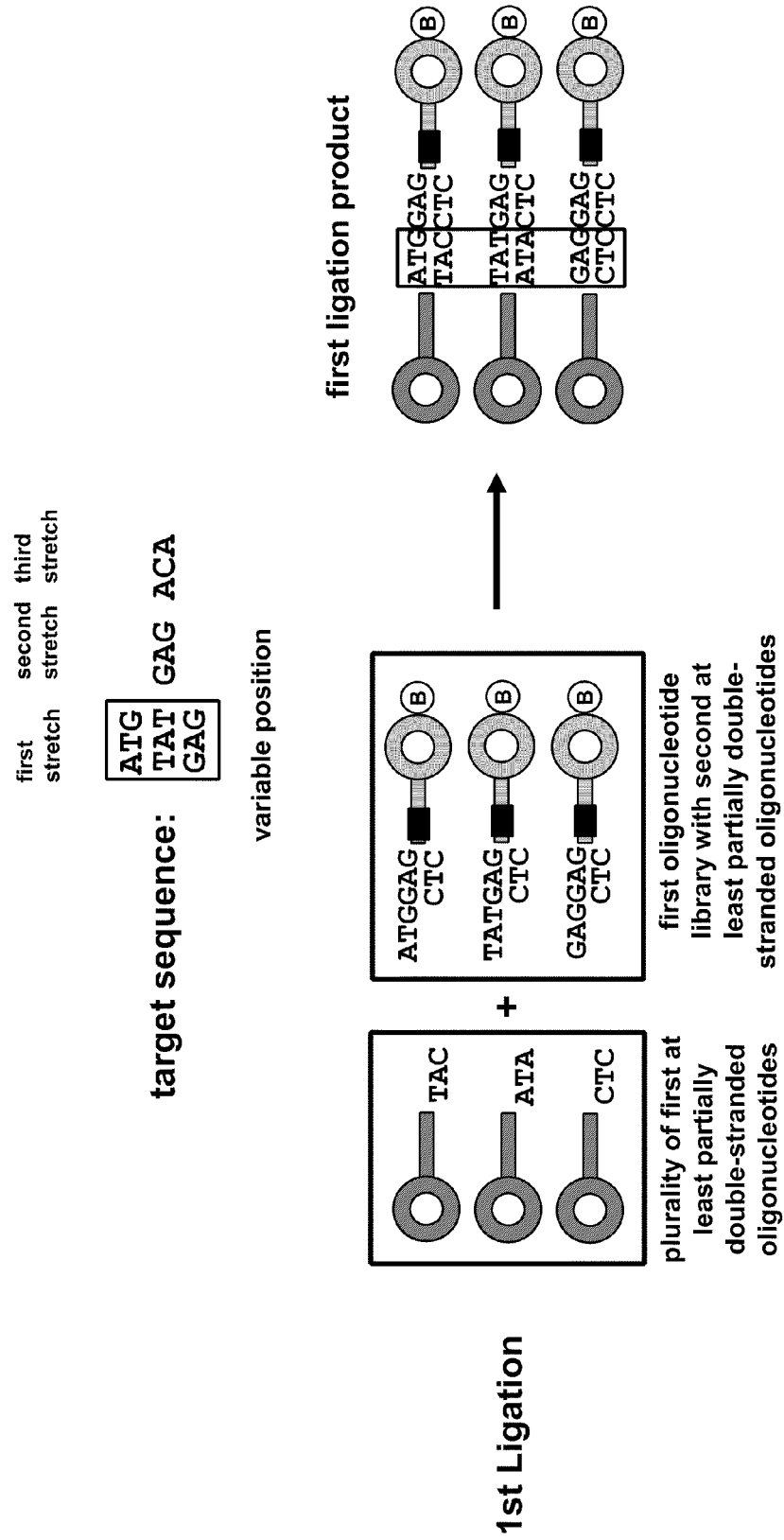

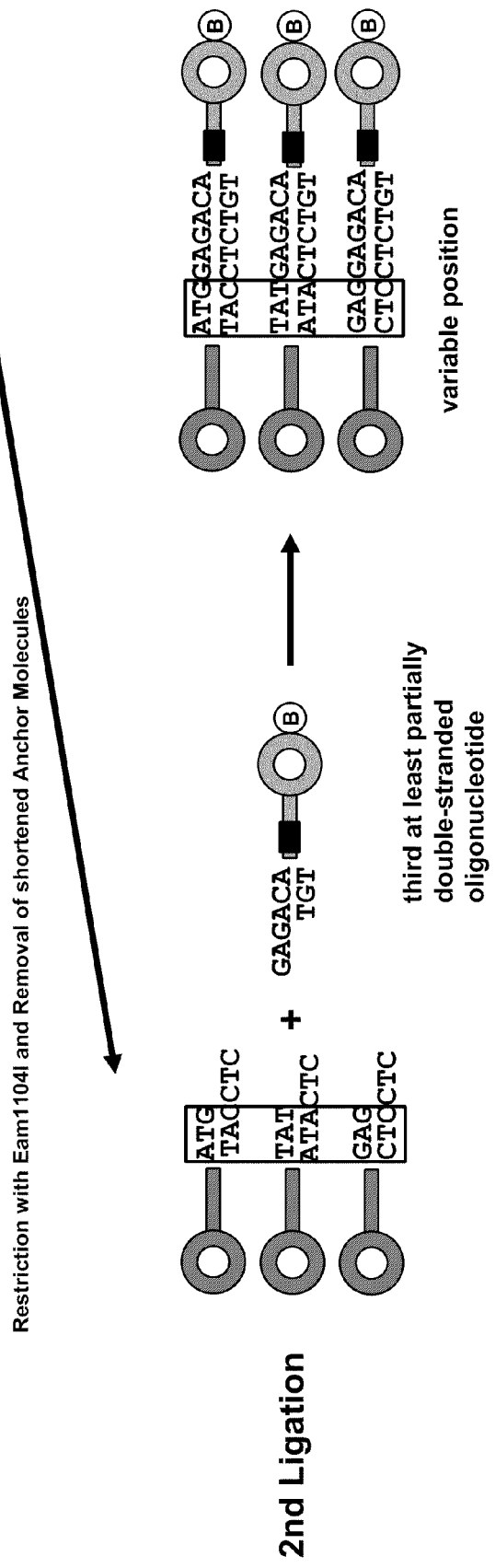
Fig. 3 (2)

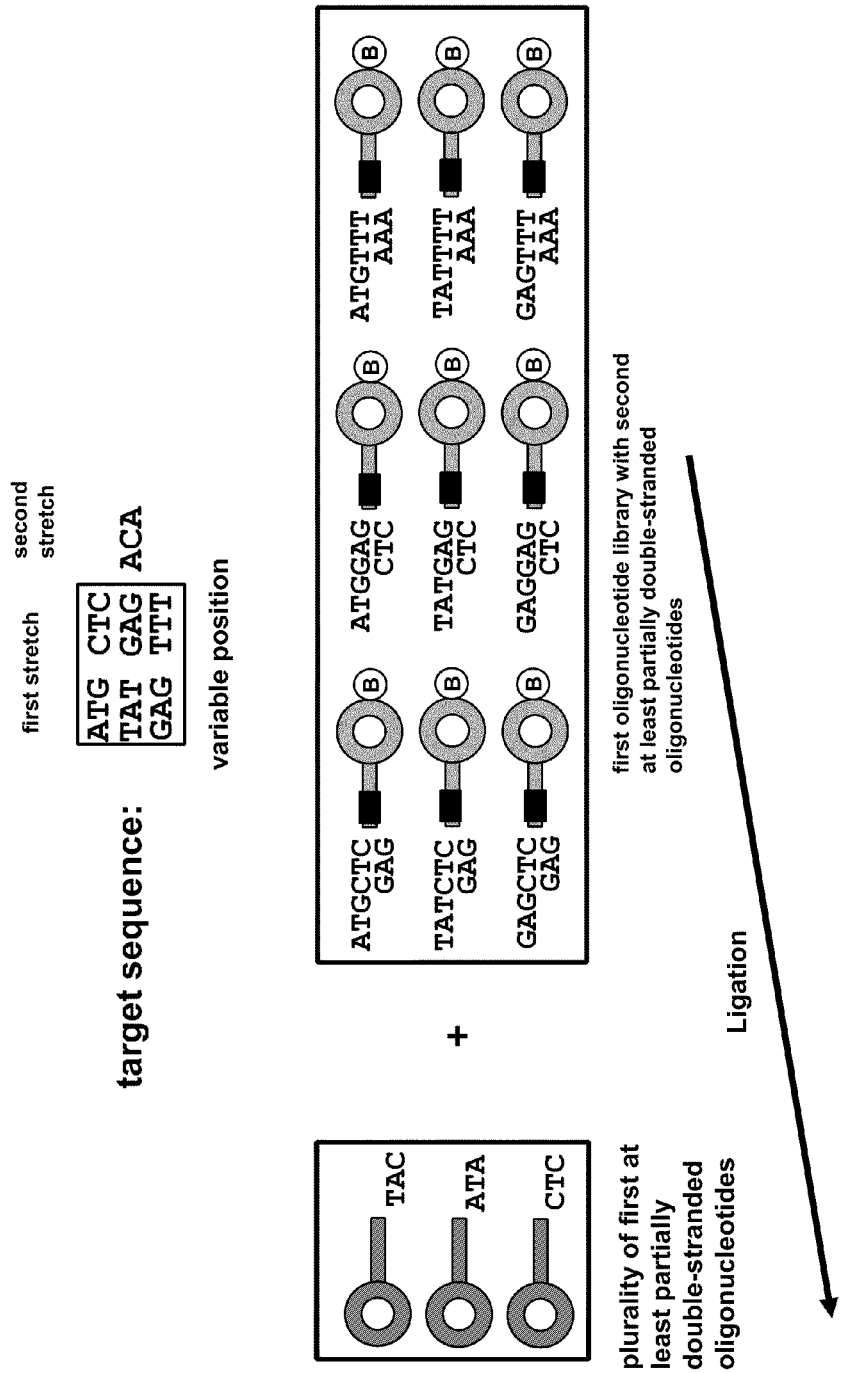

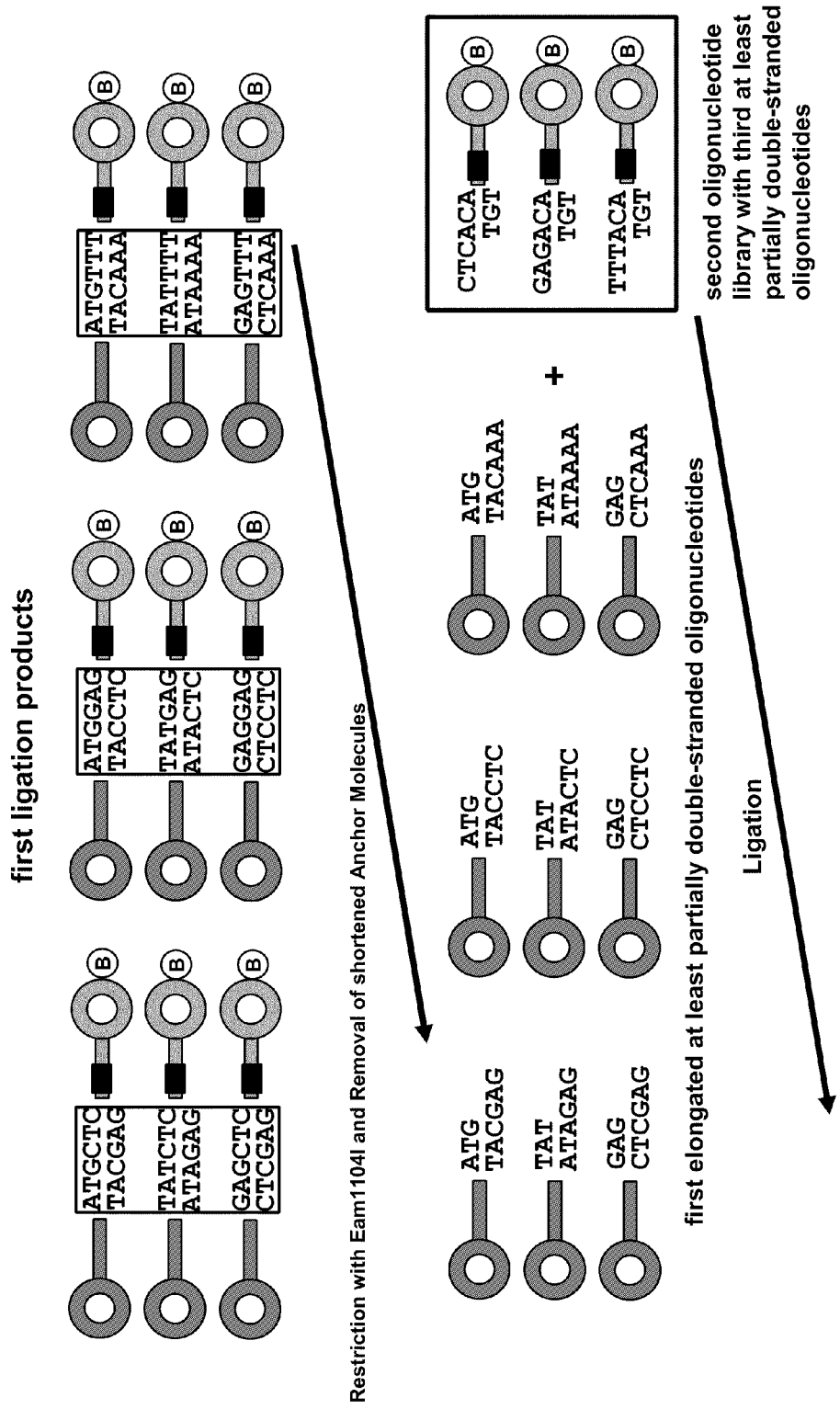
Fig. 4 (2)

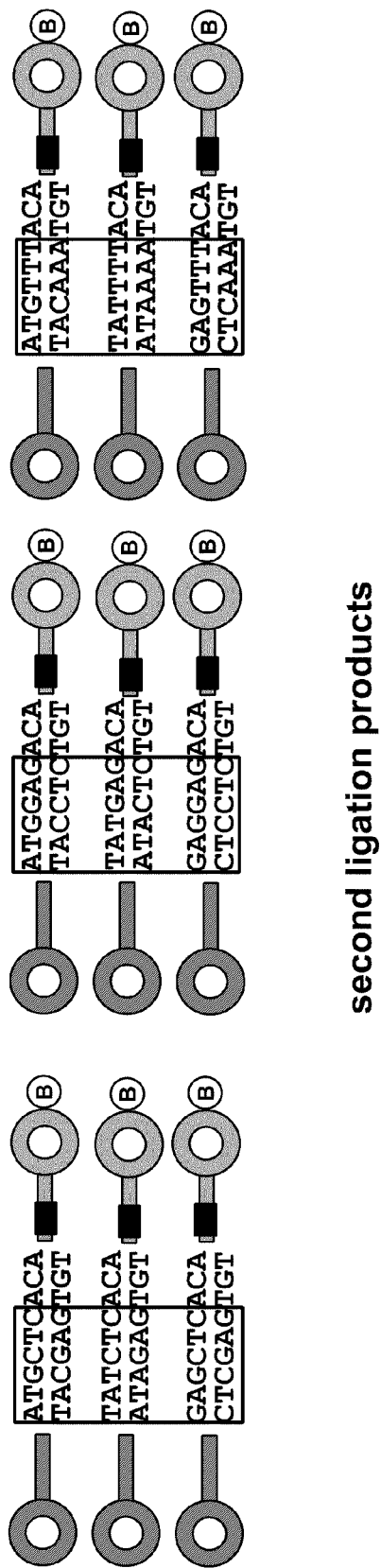
Fig. 4 (3)

SEQUENCE LISTING

```
<160> NUMBER OF SEQ ID NOS: 24

<210> SEQ ID NO 1
<211> LENGTH: 12
<212> TYPE: DNA
<213> ORGANISM: Artificial
<220> FEATURE:
<223> OTHER INFORMATION: synthetic

<400> SEQUENCE: 1
cacatggaga ca                                                            12

<210> SEQ ID NO 2
<211> LENGTH: 12
<212> TYPE: DNA
<213> ORGANISM: Artificial
<220> FEATURE:
<223> OTHER INFORMATION: synthetic

<400> SEQUENCE: 2
cactatgaga ca                                                            12

<210> SEQ ID NO 3
<211> LENGTH: 12
<212> TYPE: DNA
<213> ORGANISM: Artificial
<220> FEATURE:
<223> OTHER INFORMATION: synthetic

<400> SEQUENCE: 3
cacgaggaga ca                                                            12

<210> SEQ ID NO 4
<211> LENGTH: 12
<212> TYPE: DNA
<213> ORGANISM: Artificial
<220> FEATURE:
<223> OTHER INFORMATION: syynthetic

<400> SEQUENCE: 4
tgtctccatg tg                                                            12

<210> SEQ ID NO 5
<211> LENGTH: 12
<212> TYPE: DNA
<213> ORGANISM: Artificial
<220> FEATURE:
<223> OTHER INFORMATION: synthetic

<400> SEQUENCE: 5
tgtctcatag tg                                                            12

<210> SEQ ID NO 6
<211> LENGTH: 12
<212> TYPE: DNA
<213> ORGANISM: Artificial
<220> FEATURE:
<223> OTHER INFORMATION: synthetic
```

<400> SEQUENCE: 6
tgtctcctcg tg                                                          12

<210> SEQ ID NO 7
<211> LENGTH: 12
<212> TYPE: DNA
<213> ORGANISM: Artificial
<220> FEATURE:
<223> OTHER INFORMATION: synthetic

<400> SEQUENCE: 7
cacatgctca ca                                                          12

<210> SEQ ID NO 8
<211> LENGTH: 12
<212> TYPE: DNA
<213> ORGANISM: Artificial
<220> FEATURE:
<223> OTHER INFORMATION: synthetic

<400> SEQUENCE: 8
cactatctca ca                                                          12

<210> SEQ ID NO 9
<211> LENGTH: 12
<212> TYPE: DNA
<213> ORGANISM: Artificial
<220> FEATURE:
<223> OTHER INFORMATION: synthetic

<400> SEQUENCE: 9
cacgagctca ca                                                          12

<210> SEQ ID NO 10
<211> LENGTH: 12
<212> TYPE: DNA
<213> ORGANISM: Artificial
<220> FEATURE:
<223> OTHER INFORMATION: synthetic

<400> SEQUENCE: 10
tgtgagcatg tg                                                          12

<210> SEQ ID NO 11
<211> LENGTH: 12
<212> TYPE: DNA
<213> ORGANISM: Artificial
<220> FEATURE:
<223> OTHER INFORMATION: synthetic

<400> SEQUENCE: 11
tgtgagatag tg                                                          12

<210> SEQ ID NO 12
<211> LENGTH: 12
<212> TYPE: DNA
<213> ORGANISM: Artificial
<220> FEATURE:
<223> OTHER INFORMATION: synthetic

<400> SEQUENCE: 12
tgtgagctcg tg                                                          12

<210> SEQ ID NO 13
<211> LENGTH: 12

<212> TYPE: DNA
<213> ORGANISM: Artificial
<220> FEATURE:
<223> OTHER INFORMATION: synthetic

<400> SEQUENCE: 13
cacatggaga ca                                                          12

<210> SEQ ID NO 14
<211> LENGTH: 12
<212> TYPE: DNA
<213> ORGANISM: Artificial
<220> FEATURE:
<223> OTHER INFORMATION: synthetic

<400> SEQUENCE: 14
cactatgaga ca                                                          12

<210> SEQ ID NO 15
<211> LENGTH: 12
<212> TYPE: DNA
<213> ORGANISM: Artificial
<220> FEATURE:
<223> OTHER INFORMATION: synthetic

<400> SEQUENCE: 15
cacgaggaga ca                                                          12

<210> SEQ ID NO 16
<211> LENGTH: 12
<212> TYPE: DNA
<213> ORGANISM: Artificial
<220> FEATURE:
<223> OTHER INFORMATION: synthetic

<400> SEQUENCE: 16
tgtctccatg tg                                                          12

<210> SEQ ID NO 17
<211> LENGTH: 12
<212> TYPE: DNA
<213> ORGANISM: Artificial
<220> FEATURE:
<223> OTHER INFORMATION: synthetic

<400> SEQUENCE: 17
tgtctcatag tg                                                          12

<210> SEQ ID NO 18
<211> LENGTH: 12
<212> TYPE: DNA
<213> ORGANISM: Artificial
<220> FEATURE:
<223> OTHER INFORMATION: synthetic

<400> SEQUENCE: 18
tgtctcctcg tg                                                          12

<210> SEQ ID NO 19
<211> LENGTH: 12
<212> TYPE: DNA
<213> ORGANISM: Artificial
<220> FEATURE:
<223> OTHER INFORMATION: synthetic

<400> SEQUENCE: 19

```
cacatgttta ca                                                    12

<210> SEQ ID NO 20
<211> LENGTH: 12
<212> TYPE: DNA
<213> ORGANISM: Artificial
<220> FEATURE:
<223> OTHER INFORMATION: synthetic

<400> SEQUENCE: 20
cactatttta ca                                                    12

<210> SEQ ID NO 21
<211> LENGTH: 12
<212> TYPE: DNA
<213> ORGANISM: Artificial
<220> FEATURE:
<223> OTHER INFORMATION: synthetic

<400> SEQUENCE: 21
cacgagttta ca                                                    12

<210> SEQ ID NO 22
<211> LENGTH: 12
<212> TYPE: DNA
<213> ORGANISM: Artificial
<220> FEATURE:
<223> OTHER INFORMATION: synthetic

<400> SEQUENCE: 22
tgtaaacatg tg                                                    12

<210> SEQ ID NO 23
<211> LENGTH: 12
<212> TYPE: DNA
<213> ORGANISM: Artificial
<220> FEATURE:
<223> OTHER INFORMATION: synthetic

<400> SEQUENCE: 23
tgtaaaatag tg                                                    12

<210> SEQ ID NO 24
<211> LENGTH: 12
<212> TYPE: DNA
<213> ORGANISM: Artificial
<220> FEATURE:
<223> OTHER INFORMATION: synthetic

<400> SEQUENCE: 24
tgtaaactcg tg                                                    12
```

METHOD FOR THE PREPARATION OF A NUCLEIC ACID LIBRARY

This application claims priority under 35 U.S.C. Section 119(a) to EP 08 006 472.8 filed on Mar. 31, 2008, the contents of which are herein incorporated by reference.

The present invention is related to a method for preparing a nucleic acid library comprising a plurality of elements and a nucleic acid library thus obtainable.

De novo generation of nucleic acid molecules is increasingly used in biopharmaceutical research to replace the often quite complex cloning procedures necessary to produce desired DNA constructs with optimised properties, e.g. high level protein expression in suitable in vivo or in vitro systems. There is a variety of methods known to synthesise such DNA molecules. Practically all of these procedures rely on the synthesis, annealing and subsequent ligation of synthetic single-stranded oligonucleotides to assemble larger double-stranded DNA molecules that typically consist of more than one hundred up to several thousand base pairs. However, the efficiency of these methods is limited by several factors: (i) the quality of the oligonucleotides used, (ii) the size of the desired construct and (iii) the proportion of "difficult" sequences, e.g. those with self-complementary regions, high GC content, G tetrads, DNA kinks or repetitive sequence blocks. The oligonucleotide building blocks themselves are contaminated with various termination products and internal deletions. Especially problematic are n–1 products (oligonucleotides containing internal one nucleotide deletions occurring as a result of incomplete capping reactions), which can hardly be separated from the desired full-length oligonucleotide. As many oligonucleotides have to be assembled in order to generate a complete gene, the probability of obtaining an error-free clone, i.e. not incorporating even one defective oligonucleotide with a base change or an internal deletion approaches 0%. For example, if a gene were assembled from fifty oligonucleotides each having a purity of 90%, the probability of creating an error-free product would be roughly $0.9^{50}=0.005$. Generally, tedious error correction procedures must be employed in order to obtain a 100% error-free construct. In many cases, defective synthesis products cannot be tolerated because mistakes in the coding sequence may cause the generation of shortened transcription or translation products due to e.g. a frame shift of the open reading frame. Whereas the first two problems can be alleviated by the use of oligonucleotides of very high purity, the formation of unwanted secondary structures that may cause deletions in the synthesis product can in many cases only be suppressed if alterations are allowed in the DNA sequence.

In the prior art a variety of methods are known to produce synthetic DNA. Nearly 30 years ago, the pioneering work of Khorana and colleagues (Sekiya T, Brown E L, Belagaje R, Fritz H J, Gait M J, Lees R G, Ryan M J, Khorana H G, Norris K E. (1979), J Biol. Chem. 254(13):5781-6, and 5787-801) demonstrated the complete de novo synthesis of a suppressor tRNA gene via ligation of pairs of annealed oligonucleotides. In this and related methods, complementary single-stranded oligonucleotides comprising the complete desired DNA sequence are annealed in pairs to yield double-stranded fragments, which are aligned in the correct order by virtue of complementary single-stranded overhangs (Stabinsky, U.S. Pat. No. 4,652,639). The resulting fragments are then ligated either sequentially or in a one-tube-reaction (Jayaraman, U.S. Pat. No. 5,132,215) either enzymatically or chemically. After purification and/or cloning these gene fragments may be joined together to form larger DNA constructs. In the so-called "cassette synthesis", each pair of annealed oligonucleotides is separately cloned in a plasmid vector before joining the fragments using restriction endonucleases (Richards et al., U.S. Pat. No. 5,093,251).

Alternatively, DNA constructs can be assembled from partially annealed oligonucleotides, which after hybridisation contain single-stranded gaps that must be filled by DNA poly-merases; this method is commonly referred to as "gap filling" method. According to this method a variety of partially overlapping oligonucleotides are synthesised, purified and subsequently hybridised usually in pairs or in subgroups. After the synthesis of the respective opposite strands using a DNA polymerase the individual fragments are ligated to each other. The double stranded ligation products generated in this way may be either cloned as partial fragments or amplified in a polymerase chain reaction (PCR) with terminal oligonucleotide primers. However, this method is plagued by frequent mispriming events and internal deletions due to the formation of secondary structures.

Both methods are of limited use as with increasing length of the nucleic acid molecule to be synthesised the probability increases that one or several oligonucleotides with an incorrect sequence will be incorporated into the final product. Such errors are then copied in the DNA polymerase reaction. In addition, sequence errors may also be introduced during the PCR reaction.

A combination of the above methods is described in U.S. Pat. No. 6,472,184 in which a series of linkable oligonucleotides representing adjoining regions in one strand of the target sequence are hybridised with non-linkable oligonucleotides that are complementary to the 3' or 5' ends of the linkable oligonucleotides that are to be connected. This method is relatively simple and straightforward but is also plagued by the common problems shared by all procedures that use single-stranded oligonucleotides as building blocks: the formation of unwanted secondary structures and the incorporation of n-x oligonucleotides, which both lead to internal deletions.

Besides these standard procedures, there are further methods known in the art for the production of synthetic DNA molecules. International patent application WO 98/15567 and U.S. Pat. No. 6,110,668 teach a template-directed method of coupling oligonucleotides to yield synthetic DNA constructs by ligating a plurality of oligonucleotides that are at least partially complementary to the single-stranded template DNA and the ends of said oligonucleotides are ligated in the correct order in successive annealing and denaturation steps. However, a precondition for the application of this method is the prior existence of a suitable template DNA excluding its use in de novo synthesis.

International patent application WO 99/47536 discloses a solid phase gene synthesis method in which single-stranded oligonucleotides are sequentially ligated to an immobilised starter molecule in a defined orientation. A disadvantage of this method is that many steps are required to synthesise larger genes resulting in reduced yield and enrichment of defective sequences. Also, this method is difficult to automate which is a prerequisite for a rapid, standardised synthesis.

International patent application WO 00/75368 discloses a combinatorial solid phase synthesis of nucleic acids using a library of double-stranded oligonucleotides as standardised building blocks. The use of standardised building blocks makes it unnecessary to synthesise a new set of oligonucleotides for each new synthesis. These double-stranded library oligonucleotides generally share an identical overall structure and thus avoid common synthesis problems caused by the formation of alternative secondary structures of the oligonucleotide building blocks such as the introduction of deletions. In one preferred version, they contain a terminal loop, a double-stranded stem and a short single-stranded overhang. There are two different classes of library oligonucleotides, which are characterised by the presence of different recognition sites for type IIS restriction enzymes within their sequence and the presence or absence or the type of an internal modification. The nucleotides in the overhang and the directly adjacent region form the variable portion that actually contributes to the nucleic acid to be synthesized; the remaining sequence is generally identical in all oligonucleotides belonging to the same class.

To build up a double-stranded nucleic acid, its sequence is first broken down into smaller fragments (usually between 6 and 30 base pairs each). These so-called elongation blocks are then synthesised in parallel reactions. In one such reaction, two double-stranded library oligonucleotides, one of each class, are ligated via matching single-stranded overhangs. The ligation products thereof are subsequently cleaved with the type IIS restriction enzyme, which is specific for the oligonucleotide that donates nucleotides. The net effect of such a ligation/restriction cycle is the addition of a small number of base pairs (typically between one to five) to the starting oligonucleotide. This process is then repeated until the synthesis of the desired elongation block is completed.

In a second reaction phase, the so-called transposition, those elongation blocks that are adjacent in the nucleic acid to be synthesised are ligated in a pair wise fashion after each block has been cleaved with a different type IIS restriction enzyme. By repeating this procedure several times the length of the transposition intermediates doubles in each step whereas the number of reactions is cut in half. Thus a defined nucleic acid molecule can be generated in very few cycles. The advantage of this method resides in the combinatorial pair wise assembly of the fragments of the nucleic acid molecule to be synthesised, in a sequence independent manner. Any desired elongation block may thus be generated from a standardised nucleic acid library with a defined number of elements.

The number of the elements of such a library depends on the length of the overhangs generated by the individual type IIS restriction enzyme as well as the number of nucleotides that are added to the growing oligonucleotides in each elongation cycle.

This method offers a number of advantages: it can be completely automated since there is no need to synthesise and purify new oligonucleotides to build large genes or DNA fragments, the building blocks are prepared in a large scale and can be used to assemble many different constructs until the supply is used up thus reducing the cost for oligonucleotides by one to two orders of magnitude.

In various fields such as enzymology and antibody based therapy, however, there is a need to optimize the respective proteins, i.e. enzymes and antibodies, respectively. Typically, such optimization is performed by altering the amino acid sequence of such proteins. In case said proteins are translation products of a nucleic acid molecule, such coding nucleic acid molecule may be subject to such optimization in terms of altering the nucleic acid sequence. In the art, various approaches are described so as to manipulate the amino acid sequence of such protein and the nucleic acid sequence, respectively, coding for such protein. However, mutating the wildtype sequence is typically not sufficient so as to provide an optimized protein. Rather a set of mutated sequences providing for a set of mutated amino acid sequences and thus proteins, which are also referred to as muteins are required so as to identify the mutein(s) having the desired characteristic(s). This more heuristic approach is still promising and widely pursued although increasing data is available on the crystal structure of the target molecules of said proteins. Nevertheless, the code according to which an amino acid sequence folds and the amino acid sequence required so as to generate a distinct three-dimensional structure of the protein, is still at an early stage.

In the prior art, such muteins are generated by mutagenesis. Apart from random mutagenesis also site-specific mutagenesis is performed. Although random mutagenesis, e.g. by error-prone PCR, is a powerful means which provides at least a variety of muteins starting from a basic amino acid sequence, which is typically the wildtype amino acid sequence, the outcome of random mutagenesis is poorly predictable. Also the use of site-specific mutagenesis methods targeting a controlled level of randomisation to specific positions is not necessarily suitable to provide for a well-defined variety of such muteins (reviewed in Neylon (2004), NAR, 1448-59). At least, the generation of such variety is laborsome. Undoubtedly, the generation of a library of muteins having distinct and well-characterized mutations compared to the wildtype or starting sequence, is most desirable, since it will have a direct impact on the effort necessary to identify clones with desired characteristics in a subsequent screening process. Furthermore, it is desirable to control the composition of such library in terms of the relative representation of individual sequences. Depending on the intended use or application, such library may have an even distribution of the various sequences or a biased distribution, i.e. one where individual sequences are present with an increased or decreased frequency.

The method for synthesizing a nucleic acid as disclosed in international patent application WO 00/75368 may, of course, also be useful in generating the various nucleic acid sequences which are subsequently translated into the corresponding muteins. However, the respective library then has to be generated by pooling the individual either nucleic acid sequences or the amino acid sequences. Such procedure, although providing for the specific nucleic acid sequences and amino acid sequences, respectively, is expensive, reduces the overall yield of the process and requires quite a number of reaction steps. Additionally, when combining the various amino acid sequences and nucleic acid sequences, respectively, again an undesired biasing of individual sequences may occur.

Accordingly, there is a need in the art to provide for a method for preparing a nucleic acid library comprising a plurality of elements whereby the elements differ in at least one position which may be a single nucleotide, but may be, in case of a nucleic acid coding for an amino acid sequence, a triplet of nucleotides coding for an amino acid, whereby the amino acid thus encoded is different among at least some of the elements. More specifically, there is a need in the art for providing a method for preparing such kind of library, whereby the nucleic acid library has a distinct distribution of the various individual elements of such nucleic acid library in terms of frequency.

This and other problems are solved by the subject matter of the independent claims. Preferred embodiments may be taken from the dependent claims.

More specifically, in a first aspect the problem underlying the instant application is solved by a method for preparing a nucleic acid library comprising a plurality of elements, whereby each element of said nucleic acid library comprises a first stretch of nucleotides, a second stretch of nucleotides and a third stretch of nucleotides, whereby the sequence of the first stretch of nucleotides and of the third stretch of nucleotides are identical in each element of the nucleic acid library and the elements of the nucleic acid library differ in the sequence of the second stretch of nucleotides, whereby the method comprises the following steps:

a) providing a first at least partially double-stranded oligonucleotide having a double-stranded structure which has a single-stranded overhang, whereby the single-stranded overhang provides for a nucleotide sequence corresponding to the sequence of the first or third stretch of nucleotides of the elements of the nucleic acid library, whereby the oligonucleotide comprises a recognition site, or part thereof, for a first type IIS restriction enzyme which cuts outside its recognition site, b) providing a first oligonucleotide library comprising several members, whereby each member is a second at least partially double-stranded oligonucleotide having a double-stranded structure, whereby the second oligonucleotide comprises a recognition site, or part thereof, for a second type IIS restriction enzyme which cuts outside its recognition site, and a single-stranded overhang, whereby the single-stranded overhang or part thereof is the same for the members of the first oligonucleotide library and whereby such single-stranded overhang is essentially complementary to the single-stranded overhang of the first at least partially double-stranded oligonucleotide, whereby the double-stranded structure comprises a stretch of nucleotides whereby the members of the first oligonucleotide library differ in the sequence of said stretch of nucleotides and the sequence of the said stretch of nucleotides of the members of the first oligonucleotide library corresponds to the sequence, or part thereof, of the second stretch of nucleotides of the elements of the nucleic acid library, c) combining the first at least partially double-stranded oligonucleotide and the first oligonucleotide library and ligating one molecule of the first at least partially double-stranded oligonucleotide with one molecule of each one member of the first oligonucleotide library via their single-stranded overhangs, whereupon a first ligation product is formed, d) cutting the first ligation product with said second type IIS restriction enzyme, whereby the cleavage occurs in the nucleic acid sequence of the member of the first oligonucleotide library, whereby such cleavage provides for a plurality of first elongated at least partially double-stranded oligonucleotides and for shortened second at least partially double-stranded oligonucleotides, e) removing the shortened second at least partially double-stranded oligonucleotides, f) providing a second oligonucleotide library comprising several members, whereby each member is a third at least partially double-stranded oligonucleotide having a double-stranded structure, whereby the third oligonucleotide comprises a recognition site, or part thereof, for a third type IIS restriction enzyme which cuts outside its recognition site, and a single-stranded overhang, whereby the single-stranded overhang or part thereof is different for the members of the second oligonucleotide library and whereby such single-stranded overhangs or part thereof of the third oligonucleotide are essentially complementary to the single-stranded overhangs of the first elongated at least partially double-stranded oligonucleotides, and whereby the members of the second oligonucleotide library comprise a stretch of nucleotides in the double-stranded structure which is identical in all members and corresponds to the sequence, or part thereof, of the third or first stretch of nucleotides of the elements of the nucleic acid library, g) combining the plurality of the first elongated at least partially double-stranded oligonucleotides and the second oligonucleotide library and ligating each one molecule of the plurality of the first elongated at least partially double-stranded oligonucleotides with one molecule of each of the members of the second oligonucleotide library, whereby the single-stranded overhang of the first elongated at least partially double-stranded oligonucleotide is essentially complementary to the overhang of the third at least partially double-stranded oligonucleotide, whereupon a second ligation product is formed, h) cutting the second ligation product with the third type II S restriction enzyme, whereby the cleavage occurs in the nucleic acid sequence of the third at least partially double-stranded oligonucleotides, providing for a plurality of second elongated at least partially double-stranded oligonucleotides and shortened third at least partially double-stranded oligonucleotides, i) removing the shortened third at least partially double-stranded oligonucleotides, j) providing a fourth at least partially double-stranded oligonucleotide having a double-stranded structure which has a single-stranded overhang, whereby the single-stranded overhang provides for a nucleotide sequence essentially complementary to the single-stranded overhang of the second elongated at least partially double-stranded oligonucleotide, whereby the oligonucleotide comprises a recognition site, or part thereof, for a fourth type IIS restriction enzyme which cuts outside its recognition site, k) combining the fourth at least partially double-stranded oligonucleotide and the plurality of the second elongated at least partially double-stranded oligonucleotides and ligating one molecule of the fourth oligonucleotide and each one molecule of the plurality of the second elongated at least partially double-stranded oligonucleotides forming a third ligation product;

l) cutting the third ligation product with the fourth type IIS restriction enzyme, whereby the cleavage occurs in the nucleic acid sequence of the fourth at least partially double-stranded oligonucleotide(s), providing for a plurality of third elongated at least partially double-stranded oligonucleotides and shortened fourth at least partially double-stranded oligonucleotide, and m) removing the shortened fourth at least partially double-stranded oligonucleotide.

In an embodiment of the first aspect the method further comprises the steps of:

n) repeating steps j) to m) as steps ja) to ma), whereby the fourth at least partially double-stranded oligonucleotide of step j) is a further at least partially double-stranded oligonucleotide in step ja), the third ligation product in step k) is a further ligation product in step ka), the plurality of third elongated at least partially double-stranded oligonucleotides in step l) is a plurality of further elongated at least partially double-stranded oligonucleotides in step la), and the shortened fourth at least partially double-stranded oligonucleotide of step l) is a shortened further at least partially double-stranded oligonucleotide in step la).

In an embodiment of the first aspect after ligation step ka) the further ligation product is cleaved whereby the cleavage occurs in the nucleic acid sequence of the further elongated at least partially double-stranded oligonucleotide.

In a second aspect the problem underlying the instant application is solved by a method for preparing a nucleic acid library comprising a plurality of elements, whereby each element of said nucleic acid library comprises a first stretch of nucleotides, a second stretch of nucleotides and a third stretch of nucleotides, whereby the sequence of the first stretch of nucleotides and of the third stretch of nucleotides are identical in each element of the nucleic acid library and the elements of the nucleic acid library differ in the sequence of the second stretch of nucleotides, whereby the method comprises the following steps:

a) providing a first at least partially double-stranded oligonucleotide having a double-stranded structure which has a single-stranded overhang, whereby the single-stranded overhang provides for a nucleotide sequence corresponding to the sequence of the first or third stretch of nucleotides of the elements of the nucleic acid library, whereby the oligonucleotide comprises a recognition site, or part thereof, for a first type IIS restriction enzyme which cuts outside its recognition site, b) providing a first oligonucleotide library comprising several members, whereby each member is a second at least partially double-stranded oligonucleotide having a double-stranded structure, whereby the oligonucleotide comprises a recognition site, or part thereof, for a second type IIS restriction enzyme which cuts outside its recognition site, and a single-stranded overhang, whereby the single-stranded overhang or part thereof is the same for the members of the first oligonucleotide library and whereby such single-stranded overhang is essentially complementary to the single-stranded overhang of the first at least partially double-stranded oligonucleotide, whereby the double-stranded structure comprises a stretch of nucleotides whereby the members of the first oligonucleotide library differ in the sequence of said stretch of nucleotides and the sequence of the said stretch of nucleotides of the members of the first oligonucleotide library corresponds to the sequence, or part thereof, of the second stretch of nucleotides of the elements of the nucleic acid library, c) combining the first at least partially double-stranded oligonucleotide and the first oligonucleotide library and ligating one molecule of the first at least partially double-stranded oligonucleotide with one molecule of each one member of the first oligonucleotide library via their single-stranded overhangs, whereupon a first ligation product is formed, d) cutting the first ligation product with said second type IIS restriction enzyme, whereby the cleavage occurs in the nucleic acid sequence of the member of the first oligonucleotide library, whereby such cleavage provides for a plurality of first elongated at least partially double-stranded oligonucleotides and for shortened second at least partially double-stranded oligonucleotides, whereby such plurality of first elongated at least partially double-stranded oligonucleotides consist of various molecule species which differ in the sequence of the single-stranded overhang, e) removing the shortened second at least partially double-stranded oligonucleotides, f) providing a second oligonucleotide library comprising several subgroups of oligonucleotides and each subgroup comprising several members, whereby each member is a third at least partially double-stranded oligonucleotide having a double-stranded structure, whereby the third oligonucleotide comprises a recognition site, or part thereof, for a third type IIS restriction enzyme which cuts outside its recognition site, and a single-stranded overhang, whereby the single-stranded overhang or part thereof is different for the various subgroups of oligonucleotides of the second oligonucleotide library and whereby the single-stranded overhang, or part thereof, of each one subgroup of the second oligonucleotide library is essentially complementary to the single-stranded overhang of each one molecule species of the first elongated at least partially double-stranded oligonucleotides, and whereby the members of the second oligonucleotide library comprise a stretch of nucleotides in the double-stranded structure which is different in the members of each subgroup of the second oligonucleotide library and corresponds to the sequence, or part thereof, of the second stretch of nucleotides of the elements of the nucleic acid library, g) combining the plurality of the first elongated at least partially double-stranded oligonucleotides and the second oligonucleotide library and ligating each one molecule of the plurality of the first elongated at least partially double-stranded oligonucleotides with each one molecule of the members of the second oligonucleotide library, whereby those molecules are ligated the overhangs of which are essentially complementary to each other, whereupon second ligation products are formed, h) cutting the second ligation products with the third type II S restriction enzyme, whereby the cleavage occurs in the nucleic acid sequence of the third at least partially double-stranded oligonucleotide, providing for a plurality of second elongated at least partially double-stranded oligonucleotides and shortened third at least partially double-stranded oligonucleotides, whereby such plurality of second elongated at least partially double-stranded oligonucleotides consists of various subgroups which differ in their single-stranded overhangs, i) removing the shortened third at least partially double-stranded oligonucleotides, j) providing a third oligonucleotide library comprising several members, whereby each member is a fourth at least partially double-stranded oligonucleotide having a double-stranded structure which has a single-stranded overhang, whereby the single-stranded overhang provides for a nucleotide sequence essentially complementary to the single-stranded overhangs of the second elongated at least partially double-stranded oligonucleotides and a stretch, preferably adjacent to said overhang which is identical in the various members and provides for the third or first stretch of nucleotides of the elements of the nucleic acid library, whereby the members of the third oligonucleotide library differ in their single-stranded overhangs and the overhangs correspond to the second stretch, or part thereof, of the nucleic acid library, whereby the oligonucleotides comprise a recognition site, or part thereof, for a fourth type IIS restriction enzyme which cuts outside its recognition site, k) combining the plurality of second elongated at least partially double-stranded oligonucleotides and the third oligonucleotide library and ligating each one molecule of the members of the third oligonucleotide library with each one molecule of the plurality of the second elongated at least partially double-stranded oligonucleotides, whereby those molecules are ligated the overhangs of which are essentially complementary to each other, whereupon a third ligation product is formed;

l) cutting the third ligation product with the fourth type IIS restriction enzyme, whereby the cleavage occurs in the nucleic acid sequence of the member of the third oligonucleotide library, providing for a plurality of third elongated at least partially double-stranded oligonucleotides and shortened fourth at least partially double-stranded oligonucleotides.

m) optionally removing the shortened fourth at least partially double-stranded oligonucleotides, n) providing a fifth at least partially double-stranded oligonucleotide having a double-stranded structure which has a single-stranded overhang, whereby the single-stranded overhang provides for a nucleotide sequence essentially complementary to the single-stranded overhang of the plurality of third elongated at least partially double-stranded oligonucleotides, whereby the fifth oligonucleotide comprises a recognition site, or part thereof, for a fifth type IIS restriction enzyme which cuts outside its recognition site, o) combining the plurality of third elongated at least partially double-stranded oligonucleotides and the fourth oligonucleotide library and ligating each one molecule of the plurality of the third elongated at least partially double-stranded oligonucleotide with one molecule of the fifth at least double-stranded oligonucleotide, whereupon a fourth ligation product is formed;

p) cutting the fourth ligation product with the fifth type IIS restriction enzyme, whereby the cleavage occurs in the nucleic acid sequence of the fifth at least partially double-stranded oligonucleotide, providing for a plurality of fourth elongated at least partially double-stranded oligonucleotides and the shortened fifth at least partially double-stranded oligonucleotide, q) optionally removing the shortened fifth at least partially double-stranded oligonucleotide.

In an embodiment of the second aspect the method further comprises the steps of:

r) repeating steps n) to q) as steps na) to qa), whereby the fifth at least partially double-stranded oligonucleotide of step n) is a further at least double-stranded oligonucleotide in step na), the fourth ligation product in step o) is a further ligation product in step oa), the plurality of fourth elongated at least partially double-stranded oligonucleotides in step p) is a plurality of further elongated at least partially double-stranded oligonucleotides in step pa), and the shortened fifth at least partially double-stranded oligonucleotide of step p) is a shortened further at least partially double-stranded oligonucleotide in step pa).

In an embodiment of the second aspect after ligation step oa) the further ligation product is cleaved whereby the cleavage occurs in the nucleic acid sequence of the further elongated at least partially double-stranded oligonucleotide.

In an embodiment of the first and the second aspect the first type IIS restriction enzyme is selected from the group comprising BpiI, BbsI, Esp3I, BsmBI, Eco31I, BsaI, BfuAI, FokI, BseRI, BbvI and BsgI.

In an embodiment of the first and the second aspect the second, third, fourth, fifth and any further type IIS restriction enzyme is each and individually selected from the group comprising EarI, Eam1104I, SapI, LguI, Ksp632I and BspQI.

In an embodiment of the first and the second aspect the nucleic acid is a single-stranded nucleic acid and the length of the second stretch of nucleotides of the elements of the nucleic acid library consists of two nucleotides, three nucleotides, four nucleotides, five nucleotides, six nucleotides, seven nucleotides, eight nucleotides or multiples of three nucleotides.

In an embodiment of the first and the second aspect, wherein the nucleic acid is a double-stranded nucleic acid and the length of the second stretch of nucleotides of the elements of the nucleic acid library consists of two nucleotides, three nucleotides, four nucleotides, five nucleotides, six nucleotides, seven nucleotides, eight nucleotides or multiples of three nucleotides.

In an embodiment of the first and the second aspect the second stretch of nucleotides of the elements of the nucleic acid library is coding for one or several amino acids.

In an embodiment of the first and the second aspect the second at least partially double-stranded oligonucleotide, the third at least partially double-stranded oligonucleotide, the fourth at least partially double-stranded oligonucleotide, the fifth and the further at least partially double-stranded oligonucleotide comprises a modification, whereby such modification allows for the immobilization of the oligonucleotide to a surface.

In an embodiment of the first and the second aspect the modification is selected from the group comprising a biotin residue, a digoxigenin residue, a fluorescein isothiocyanate residue, an amino compound or a succinyl ester.

In an embodiment of the first and the second aspect the nucleic acid library is a library of a nucleic acid molecules coding for a functional nucleic acid, whereby such nucleic acid is selected from the group comprising aptamers, promoters, ribozymes, and RNAi mediating molecules In an embodiment of the first and the second aspect the nucleic acid library is a library of nucleic acid molecules coding for a peptide, polypeptide or protein.

In an embodiment of the first and the second aspect the peptide, polypeptide and protein is selected from the group comprising peptide aptamers, enzymes, restriction enzymes, DNA binding domains, vaccines, antibodies, pharmaceutically active proteins, anticalines, DARPins, nanobodies, and AdNectines.

In an embodiment of the first and the second aspect the nucleic acid library is a library of nucleic acid molecules coding for a polypeptide, whereby the polypeptide is a scaffold comprising one or several constant regions, whereby one or several variable regions and one or several of the variable regions is/are encoded by the sequence of the second stretch of nucleotides of the elements of the nucleic acid library.

In an embodiment of the first and the second aspect the second stretch of nucleotides of the elements of the nucleic acid library is the only difference between said elements.

In a third aspect the problem underlying the instant application is solved by a nucleic acid library obtainable by a method according to the first and/or second aspect.

In an embodiment of the third aspect the members of the library differ in a nucleotide position, whereby such nucleotide position comprises at least 1, 2, 3, 4, 5, and 6 nucleotides.

In a fourth aspect the problem underlying the instant application is solved by a method for the manufacture of a nucleic acid molecule library, whereby the nucleic molecule library comprises a plurality of elements, whereby the elements comprise at least one constant stretch and at least one variable stretch and whereby the at least one constant stretch comprises a nucleotide sequence which is the same in all of the elements, and the at least one variable stretch comprises a nucleotide sequence which is different in all of the elements, whereby the method comprises the following steps:

a) providing a first oligonucleotide, whereby the first oligonucleotide is either an at least partially double-stranded oligonucleotide having a single-stranded overhang and comprising a recognition site for a first type IIS restriction enzyme which cuts outside its recognition sequence, or a nucleic acid library comprising a plurality of elements, whereby the nucleic acid library is the nucleic acid library according to the first, second and/or third aspect and the elements of the nucleic acid library have a single-stranded overhang, and the elements of the nucleic acid library comprise a recognition site for a first type IIS restriction enzyme which cuts outside its recognition sequence;

b) providing a second oligonucleotide, whereby such second oligonucleotide is a nucleic acid library comprising a plurality of elements, whereby the nucleic acid library is the nucleic acid library according to any of the first, second and/or third aspect and the elements of the nucleic acid library have a single-stranded overhang which is at least partially complementary to the single-stranded overhang of the oligonucleotide provided in step a), the elements of the nucleic acid library comprise a recognition site for a second type IIS restriction enzyme which cuts outside its recognition sequence, whereby the second type IIS restriction enzyme of the elements of the nucleic acid library is different from the first type IIS restriction enzyme of the oligonucleotide provided in step a);

c) combining the oligonucleotides of step a) and step b) and ligating one molecule of the oligonucleotide of step a) with each one molecule of each one element of the nucleic acid library of step b) via their single-stranded overhangs under the proviso that the oligonucleotide of step a) is different from the nucleic acid library according to any of the first, second and/or third aspect; or combining the oligonucleotides of step a) and step b) and ligating each one molecule of each one element of the nucleic acid library of step a) with each one molecule of each one element of the nucleic acid library of step b) via their single-stranded overhangs under the proviso that the oligonucleotide of step a) is a nucleic acid library according any of the first, second and/or third aspect;

d) optionally removing non-reacted reactants and enzymes, e) cleaving the ligation product of step c) with a type IIS restriction enzyme which cuts outside its recognition sequence, whereby the cleavage occurs in the oligonucleotide of step a) or step b) providing for a library of extended nucleic acid molecules; and f) optionally separating the extended nucleic acid molecules from the reaction mixture.

In an embodiment of the fourth aspect the step a) to f) are repeated under the provisos that the oligonucleotide of step a) is a fourth oligonucleotide which is either a library of extended nucleic acid molecules provided in step e), or a fourth at least partially double-stranded oligonucleotide having a single-stranded overhang and comprising a recognition site for a fourth type IIS restriction enzyme which cuts outside its recognition sequence;

the oligonucleotide of step b) is a third oligonucleotide which is a library of extended nucleic acid molecules provided in step e), whereby the third and the fourth oligonucleotide each comprise a single-stranded overhang and whereby both overhangs are at least partially complementary to each other;

when combining the oligonucleotides of step a) and step b) and ligating one molecule of the oligonucleotide of step a) with each one molecule of each one element of the nucleic acid library of step b) via their single-stranded overhangs, the oligonucleotide of step a) is different from the library of extended nucleic acid molecules of step b); or when combining the oligonucleotides of step a) and step b) and ligating each one molecule of each one element of the nucleic acid library of step a) with each one molecule of each one element of the nucleic acid library of step b) via their single-stranded overhangs, the oligonucleotide of step a) is the library of extended nucleic acid molecules of step b); and wherein in step e) a further library of extended nucleic acid molecules is obtained.

In an embodiment of the fourth aspect the variable stretch or part thereof is provided by the second stretch of the elements of the nucleic acid library according to any of the first, second and/or third aspect.

In an embodiment of the fourth aspect the constant stretch or part thereof is provided by the first stretch and/or the third stretch of the elements of the nucleic acid library as described in any of the first, second and/or third aspect.

In an embodiment of the first, second and/or third aspect the ratio of the various elements and members of the libraries used in any such method is equimolar.

In an embodiment of the first, second and/or third aspect the ratio of the various elements and members of the libraries used in any such method is non-equimolar or biased.

The present inventors have surprisingly found that it is possible to use the method described in international patent application WO 00/75368 for preparing a nucleic acid library comprising a plurality of elements, whereby the various elements or nucleic acid molecules differ, in a controlled manner, at one or several distinct nucleotide positions. Preferably, the library has a defined composition, i.e. the individual elements of the library, i.e. the various nucleic acid sequences are contained in the library with a defined, preferably controlled frequency. It will be understood that the individual nucleic acid sequence which is also referred to herein as an element of the nucleic acid library, as nucleic acid species, is as such at least one time, preferably several times present in the library.

Insofar, the present inventors have departed from the basic concept underlying the method described in international patent application WO 00/75368 which explicitly provides for a single defined nucleic acid sequence and thus a defined amino acid sequence if such nucleic acid sequence is a coding nucleic acid sequence, which is preferably the case. Given the meticulousness of said method, it was not obvious for the present inventors to use such method and modify it so as to provide a nucleic acid library as defined herein. It is the merit of the present inventors that they have modified the method as described in international patent application WO 00/75368 in a way to prepare a nucleic acid library in accordance with the present invention, with the advantages as inherent to the method of WO 00/75368 being mirrored in the method of the present invention insofar as the individual sequences, i.e. the individual element of the library are provided with the required meticulousness while at the same time a composition of the library is provided which is well defined and actually controlled in terms of the frequency with which the individual elements and more specifically the individual nucleic acid species are present in said library. Insofar, despite providing for a sequence diversity being reflected as a nucleic acid library comprising a plurality of elements, the method according to the present invention provides the advantages inherent to international patent application WO 00/75368 in terms of quality, yield and reliability of the nucleic acid sequences to be synthesized.

The method according to the present invention is advantageously used for the design of proteins and more specifically the optimisation of proteins through selection of an optimised protein species out of a variety of muteins. The field of use of such libraries and muteins, respectively, resides in industrial enzymes in the field of food, feed, biofuel and the like and in the manufacture of therapeutic proteins like antibodies, nanobodies, scaffolds such as anticalines, DARPins and AdnEC-TINEs (reviewed in Binz et al. (2005), Nature Biotechnology, 1257-68) and peptide aptamers as, e.g., described in Crawford M et al., Briefings in Functional Genomics and Proteomics, Vol. 2, No. 1, 72-79, April 2003. A further field of use is the optimisation of vaccines, optimisation and production of biopharmaceuticals, optimisation of restriction enzymes, manufacture of specific DNA binding domains and optimisation of metabolic pathways. It will, however, be acknowledged by the person skilled in the art that the application of the methods according to the invention are not limited thereto.

Although it is evident that the present invention is particularly advantageous in creating a library of nucleic acid sequences which encode for a variety of proteins, whereby such variety of proteins differ in one or several amino acid positions compared to a starting material which is preferably the wildtype sequence, it is within the present invention that the nucleic acid library prepared in accordance with the present invention, may be used for non-coding nucleic acids. Preferably, such non-coding nucleic acids are aptamers as, for example, described in European patent EP 0 533 838, promoters, ribozymes, single-stranded and double-stranded RNA and RNAi constructs.

It will be acknowledged that the reaction products of the method according to the present invention are typically elongation products, particularly elongation products in the sense of international patent application WO 00/75368, which can be further used, particularly used in the second reaction phase, i.e. the so-called transposition, of the method according to international patent application WO 00/75368. Preferably, the reaction product provided by the method according to the present invention, is one element of a pair of nucleic acid molecules which is used in a pair-wise fashion and such nucleic acid molecules differ at least in a single-stranded overhang which allows the ligation of said two molecules.

Any of the at least partially double-stranded oligonucleotides used in connection with the methods according to the instant application, if not explicitly indicated to the contrary herein, can be either formed of a single oligonucleotide, whereby the double-stranded stretch thereof is formed by a part of the oligonucleotide folded back onto another part of the oligonucleotide, or it can be formed of two or several oligonucleotides. In the latter case, it is sufficient that the double-stranded stretch of said oligonucleotide is formed, mostly irrespective of how many individual oligonucleotides are involved in the reaction. However, it is preferred that said oligonucleotide is formed by two oligonucleotides which are annealed to each other, preferably through Watson-Crick base pairing. It is also within the scope of the present invention that said oligonucleotide is formed by a branched oligonucleotide. Again such branched oligonucleotide is suitable for the use in the method according to the first aspect of the present invention provided that it meets the criteria as defined in step a) of said method. The branched oligonucleotide can either be generated by joining an at least partially double-stranded oligonucleotide and a single-stranded oligonucleotide, or from the two or several single-stranded oligonucleotides base-pairing to form said at least partially double-stranded oligonucleotide having a single-stranded protrusion or overhang. The branch point is a nucleotide, which is preferably located in the loop region, and which has a chemical moiety which allows for the chemical coupling of a further nucleotide or oligonucleotide thereto. Such chemical moieties which allow for the branching of an oligonucleotide or a nucleic acid, respectively, are known to the ones skilled in the art. Examples for such chemical moieties are amino or carboxy linkers that can be activated with EDC (1-ethyl-3-(3-dimethylaminopropyl) carbodiimide) and NHS(N-hydroxysulfosuccinimide) described by Hoare and Koshland jr. (Hoare D G, Koshland D E, Jr. (1967), J. Biol. Chem. 242: 2447-2453) and Johnsson et al. (Johnsson B, Lofas S, Lindquist G. (1991), Anal Biochem. 198:268-77.), respectively. Said first oligonucleotide of step a) is also referred to herein as "left starter", whereas the analogous first oligonucleotide of step b) is also dubbed "right starter".

About the length of the various overhangs as described herein, such length is preferably selected from the group comprising a 1 nucleotide overhang, a 2 nucleotide overhang, a 3 nucleotide overhang, a 4 nucleotide overhang or a 5 nucleotide overhang. As a general rule, the length of the overhang is determined by the restriction enzyme(s) used in the elongation phase, i.e. the first step of the method for the manufacture of a nucleic acid. The nucleotides of the single-stranded overhang plus the adjacent nucleotides distal from the cleavage site of the restriction enzyme specific for the second at least partially double-stranded oligonucleotide make up the nucleotides that are transferred in each elongation step. The number of transferred nucleotides in turn determines the size of the library of oligonucleotides necessary to build every possible sequence. For instance, if six nucleotides are transferred in each step, then a library of 4⁶=4096 different oligonucleotides will be required to represent all possible hexamer permutations. It will be acknowledged that a particularly preferred overhang in connection with the methods of the present invention consists of 3 nucleotides, whereby such 3 nucleotides encode for an amino acid.

In an embodiment, the modification of the oligonucleotides used in connection with the method according to the present invention, is one element of a specific interaction pair such as biotin and avidine, streptavidine, extravidine and any mutant or derivative thereof, including artificial biotin binding sites. Further specific interaction pairs include, however are not limited thereto, FITC—anti-FITC antibodies (Serke S, Pachmann K (1988), J Immunol Methods. 112(2):207-11) and digoxigenin—anti-digoxigenin antibodies (Kessler C, Holtke H J, Seibl R, Burg J, Muhlegger K. (1990), Biol Chem Hoppe Seyler. 371(10):917-27).).

It will also be acknowledged by a person skilled in the art that such modification may be a nucleotide or nucleotide sequence which allows for a specific immobilisation to a surface.

In connection with the type IIS restriction enzymes, the following combinations are, in principle, suitable for carrying out the present invention.

One group of type IIS restriction enzymes which is preferably used as the first type IIS restriction enzyme in connection with the methods of the present invention, comprises the following enzymes: BpiI, BbsI, Esp3I, BsmBI, Eco31I, BsaI, BfuAI, FokI, BseRI, BbvI and BsgI.

Another group of type IIS restriction enzymes which is preferably used as the second, third, fourth, fifth and further type IIS restriction enzyme in connection with the methods of the present invention, comprises the following enzymes: EarI, Eam1104I, SapI. LguI, Ksp632I and BspQI. In connection with this group restriction enzyme1104I is particularly preferred.

The present invention is now further illustrated by referring to the attached figures from which further features, embodiments and advantages may be taken.

FIG. 1 shows an illustration of the method for the preparation of a nucleic acid library according to the first aspect of the present invention, whereby the members of the nucleic acid library differ at one position of the sequence and such one position provides for one different amino acid upon translation, FIG. 1(1) shows a target sequence, which includes SEQ ID NOs 1-3, respectively, in order of appearance. FIG. 1(2) shows a 3$^{rd}$ Ligation, wherein the variable position of the third ligation product is SEQ ID NOs 1, 4, 2, 5, 3 and 6, respectively, in order of appearance. FIGS. 1(1)-1(2) show single and double stranded nucleic acid sequences. The single stranded nucleic acid sequences are read from left to right. For the double stranded nucleic acid sequences, the upper strand is read from left to right, and the lower strand is read from right to left.

FIG. 2 shows an illustration of the method for the preparation of a nucleic acid library according to the second aspect of the present invention, whereby the members of the nucleic acid library differ at one position of the sequence and such position comprises two consecutive triplets of nucleotides each coding for an amino acid. FIG. 2(1) shows a target sequence, which includes SEQ ID NOs 7-9, respectively, in order of appearance. FIG. 2(3) shows third ligation products, which include SEQ ID NOs 7, 10, 8, 11, 9, 12, 13, 16, 14, 17, 15, 18, 19, 22, 20, 23, 21, and 24, respectively, in order of appearance. FIGS. 2(1)-2(3) show single and double stranded nucleic acid sequences. The single stranded nucleic acid sequences are read from left to right. For the double stranded nucleic acid sequences, the upper strand is read from left to right, and the lower strand is read from right to left.

FIG. 3 shows an illustration of the method for the preparation of a nucleic acid library according to the first aspect of the present invention, whereby the members of the nucleic acid library differ at one position of the sequence and such one position provides for different amino acids upon translation, whereby the variable position is a terminal position. FIGS. 3(1)-3(2) show single and double stranded nucleic acid sequences. The single stranded nucleic acid sequences are read from left to right. For the double stranded nucleic acid sequences, the upper strand is read from left to right, and the lower strand is read from right to left.

FIG. 4 shows an illustration of the method for the preparation of a nucleic acid library according to the second aspect of the present invention, whereby the members of the nucleic acid library differ at two positions of the sequence and such two positions provide for two different amino acids upon translation, whereby the variable positions are two consecutive terminal position. FIGS. 4(1)-4(3) show single and double stranded nucleic acid sequences. The single stranded nucleic acid sequences are read from left to right. For the double stranded nucleic acid sequences, the upper strand is read from left to right, and the lower strand is read from right to left.

Figure 7:
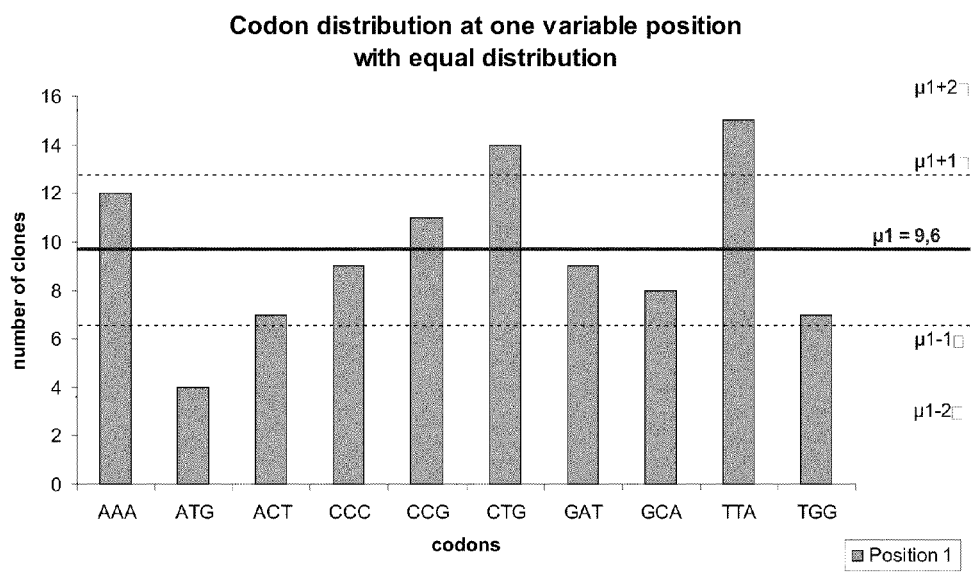
Figure 8:
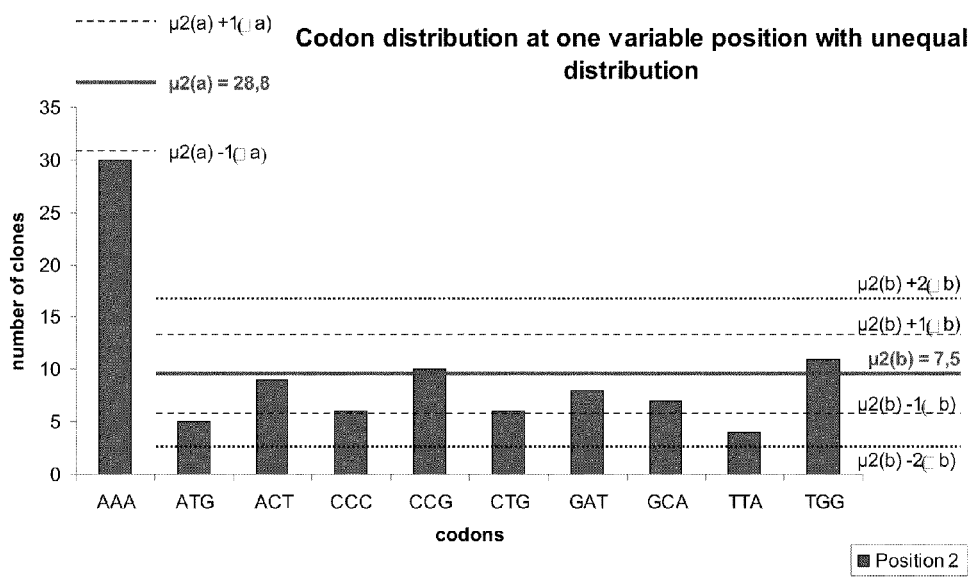

FIG. 7 is a histogram indicating the codon frequencies at one variable position with equal distribution of the codons obtained in the synthesis of a nucleic acid library using the method according to the first aspect of the instant application; and FIG. 8 is a histogram indicating the codon frequencies at one variable position with unequal distribution of the codons obtained in the synthesis of a nucleic acid library using the method according to the first aspect of the instant application.

It will be acknowledged by a person skilled in the art that the following is a description of the methods according to the present invention for preparing a nucleic acid library comprising a plurality of elements, whereby only the essential steps are described in more detail. Further details on the performing of the method according to the present invention are obvious to a person skilled in the art in the light of the disclosure of the instant application and the underlying reaction principles which are based on the method as defined in international patent application WO 00/75368.

Method for Preparing a Nucleic Acid Library as Illustrated in FIGS. 1(1) and 1(2).

The method of the present invention is described in relation to the synthesis of a target sequence which is depicted in FIG. 1(1). Such target sequence comprises four triplets, whereby, reading from left to right, which is typically in the 5'→3' direction, the second triplet is varied both at the nucleic acid level as well as, and in particular, the amino acid level. The first, third and fourth triplet are the same for the various elements of the nucleic acid library to be prepared as are, preferably the other not specifically represented nucleotides and preferably triplets and thus amino acid sequence(s) to be synthesized in accordance with the method according to the present invention.

The nucleic acid library according to the present invention comprises a plurality of elements, whereby each element of said nucleic acid library comprises a first stretch of nucleotides which corresponds to the first triplet, a second stretch of nucleotides which corresponds to the second triplet and a third stretch of nucleotides which corresponds to the third and fourth triplet. The sequence of the first stretch of nucleotides and of the third stretch of nucleotides are identical in each element of the nucleic acid library and the elements of the nucleic acid library differ in the sequence of the second stretch of nucleotides. In the target sequence, the first stretch is thus a stretch comprising CAC, and the third stretch is a stretch comprising the two triplets GAG and ACA. The second stretch is, accordingly, the one which comprises either ATG, TAT or GAG. As outlined above, the elements of the nucleic acid library differ at least with regard to the second stretch. Accordingly, in a preferred embodiment the library according to the present invention comprises three elements, with the first element comprising the sequence of CACATGGAGACA (SEQ ID NO: 1), the second element comprising the sequence of CACTATGAGACA (SEQ ID NO: 2), and the third element comprising the nucleic acid sequence CACGAGGAGACA (SEQ ID NO: 3). It will, however, be understood that the second stretch may comprise further alternative triplets thus adding to the complexity of the nucleic acid library.

In step 1, a first at least partially double-stranded oligonucleotide having a double-stranded structure is provided. Such at least partially double-stranded oligonucleotide has a single-stranded overhang and is also referred to herein as splinker. The single-stranded overhang provides for a nucleotide sequence corresponding to the sequence of the first or the third stretch of nucleotides, or part thereof, of the elements of the nucleic acid library. If the single-stranded overhang corresponds to a part of the first or third stretch, such correspondence is preferably to the most terminal part(s) of the first and third stretch, respectively. As preferably used herein, the term that sequences correspond to each other means that the sequences are complementary to each other, preferably based on Watson-Crick base pairing, the sequences are complementary to each other, preferably completely complementary, i.e. show a perfect fit. In a preferred embodiment, the oligonucleotide comprises a recognition site or part thereof for a first type IIS restriction enzyme which cuts outside its recognition site. In the present case, such first at least partially double-stranded oligonucleotide has a single-stranded overhang comprising GTG and is thus complementary to the first triplet and thus the first stretch of the target sequence. The first at least partially double-stranded oligonucleotide consists in the embodiment depicted in FIG. 1 (1) of a single oligonucleotide which is formed by a part of such single oligonucleotide folding back to another part of the oligonucleotide thus forming a loop. However, it is also within the present invention that the at least partially double-stranded oligonucleotide is formed by two separate single-stranded oligonucleotides base-pairing to each other thus generating such at least partially oligonucleotide and the afore-described single-stranded overhang. In a preferred embodiment, the end of such latter at least partially double-stranded oligonucleotide which is not providing the single-stranded overhang required for ligation is blocked so as to avoid any ligation or reaction as potentially possible in the subsequent steps of the method according to the present invention.

In step 2, a first oligonucleotide library is provided which comprises several members. Each member of said first oligonucleotide library is also referred to herein as a second at least partially double-stranded oligonucleotide and has a double-stranded structure. The double-stranded structure may, as in connection with the first at least double-stranded oligonucleotide, be formed by two single strands having the further modification as described above. The members of the first oligonucleotide library comprise a recognition site, or part thereof, for a second type IIS restriction enzyme which cuts outside its recognition site. Furthermore, such second at least partially double-stranded oligonucleotide provides for a single-stranded overhang. The members of the first oligonucleotide library have the same single-stranded overhang and such single-stranded overhang is essentially or partially complementary to the single-stranded overhang of the first at least partially double-stranded oligonucleotide. In the present case, such single-stranded overhang is CAC. Subsequent to the single-stranded overhang, the second at a partially least double-stranded oligonucleotides comprise a double-stranded structure which comprises a stretch of nucleotides, whereby the members of the first oligonucleotide library differ in the sequence of said stretch of nucleotides and the sequences of the said stretch of nucleotides correspond to the sequences, or part thereof, of the second stretch of the elements of the nucleic acid library according to the present invention. Accordingly, as depicted in FIG. 1 (1), a first oligonucleotide library is provided where the double-stranded part of the members subsequent to the single-stranded overhang comprises the various sequences subject to the second stretch of the nucleotides of the elements of the nucleic acid library. It is within the present invention that the double-stranded structure comprises further nucleotides which, in an embodiment, may or may not contain further nucleotides of the target sequence. In the particular use depicted in FIG. 1(1), these sequences are ATG, TAT and GAG which are base-pairing to their complementary sequences, i.e. TAC, ATA and CTC (in 3'→5' direction) which may also be represented herein as ATG/TAC, TAT/ATA and GAG/CTC. The members of the first oligonucleotide library differ thus in the sequence of said stretch of nucleotides and the sequence of said stretch of nucleotides of the members of the first nucleotide library correspond to the sequence or part thereof of the second stretch of nucleotides of the elements of the nucleic acid library. Accordingly, the complexity of the nucleic acid library to be prepared using the method according to the present invention, which in the case of FIG. 1(1) is three, i.e. consists of three different elements, is reflected and preferably actually the same as the complexity of the first oligonucleotide library, which also consists of three different members.

Additionally, the members of the first oligonucleotide library comprise a modification. In the present case such modification allows the immobilization of the various members to a surface, typically a surface of a support or a carrier. The immobilization is specifically mediated by an interaction between the modification and an interaction partner of such modification. In the present case, the modification is biotin which is interacting with streptavidine as its interaction partner and provides for a stable complex allowing the immobilization of the members of the first oligonucleotide library and the reaction products of any ligation reaction using the same. The members, because of the presence of the modification, are also referred to herein as anchors or anchor molecules.

In FIG. 1(1) the recognition site for the type IIS restriction enzyme of the members of the first oligonucleotide library is indicated as a black box illustrating the fact that for this kind of restriction enzyme the recognition site is lying outside of the cleavage site.

In step 3 the first at least partially double-stranded oligonucleotide and the first oligonucleotide library and the members thereof, respectively, are combined. Upon such combining, one molecule of the first at least partially double-stranded oligonucleotide anneals and is subsequently ligated to one molecule of one member of the first oligonucleotide library, preferably by means of a ligase or ligase activity. Such ligation occurs upon forming a first pre-ligation product through the hybridisation of the single-stranded overhangs of the two kinds of molecules, with such overhangs acting as "sticky ends". The reaction product of the ligation is referred to as the first ligation product. Due to the first oligonucleotide library comprising various elements and species, respectively, the ligation reaction results in a pool of first ligation products or a plurality of first ligation products. Also in this plurality of ligation products, which actually constitutes a further library, the members differ at least and preferably only, in the present example, in the sequence corresponding to the second triplet and thus the second stretch of the target sequence, whereas typically the remainder of the first ligation product in terms of nucleotide sequence is preferably the same for the various elements of the thus formed first ligation product library. The plurality of first ligation products comprises in the instant case three different ligation products as determined by the number of the different second at least partially double-stranded oligonucleotides forming the first oligonucleotide library. It is to be acknowledged that in the method according to the first aspect, the first ligation product comprises various species of molecules which differ in their sequence corresponding to the second stretch of the target sequence. The nucleic acid sequence variety of such species is provided by the first oligonucleotide library.

In step 4, the first ligation products are cut with a type IIS restriction enzyme. Such type IIS restriction enzyme's recognition site is the one provided by the second at least partially double-stranded oligonucleotides and is referred to herein as second type IIS restriction enzyme. The cutting of the first ligation products is performed on the pool and library, respectively, consisting of the first ligation products. Accordingly, the cutting or cleavage of the first ligation products results in a plurality of thus cut molecules, whereby the reaction product of such cutting is a plurality of first elongated at least partially double-stranded oligonucleotides consisting of different species of first elongated at least partially double-stranded oligonucleotides and a plurality of shortened second at least partially double-stranded oligonucleotides.

It will be acknowledged that the performance of step 3 and 4, respectively, can be carried out under different reaction conditions in terms of immobilizing or non-immobilizing the members of the first oligonucleotide library consisting of the first library ligation product, respectively. In each case, the respective molecules provide for a modification which, as outlined above, allows for immobilization of the molecules to a support comprising the interaction partner of the modification. Accordingly, any sequence with reference to an immobilization step can, in principle, be performed in various embodiments. Accordingly, it is within the present invention to perform the ligation reaction subject to step 3 in a liquid phase, i.e. with the members of the first oligonucleotide library not being immobilized. Subsequently, the cutting of the first ligation product may occur. In an embodiment, such cutting is then also performed in the liquid phase with the first ligation product not being immobilized to a support via its modification. After the cutting the shortened second at least partially double-stranded oligonucleotide is removed from the reaction mixture via its modification by binding to the support. Alternatively, after the ligation, the first ligation product can be immobilized to a surface and the cutting of the first ligation product is performed with the first ligation product being immobilized to such surface. In any case, the shortened second at least partially double-stranded oligonucleotide is ultimately removed from the reaction by immobilizing it through its modification to a support. It will be acknowledged that due to the modification allowing a specific interaction with its interaction partner such as biotin with streptavidin, for immobilization purposes the reaction is transferred to a reaction vessel, preferably the walls of the which constituting a support contain the interaction partner of the modification, in the present example given the modification being biotin, streptavidin. Due to the high affinity of biotin and streptavidin, the binding of the molecule containing the modification to the support occurs immediately. In other words, if a reaction such as the ligation reaction is to be performed with a molecule having such modification, the reaction vessel or any surface available in such reaction is not to comprise an interaction partner of the modification, whereas in case immobilisation is intended, a reaction vessel is used the surface of which provides for such interaction partner of the modification, either by the reaction vessel or by other surfaces prevalent in such reaction.

In other words, in one embodiment of the method according to the first aspect upon formation of the ligation product it is possible to cutting the ligation product with the respective type IIS restriction enzyme the recognition sequence of which is provided by the respective oligonucleotide library or any oligonucleotide which provides for a modification which allows the immobilization of the ligation product to a support, whereby the cutting provides for a plurality of elongated at least partially double-stranded oligonucleotides and shortened at least partially double-stranded oligonucleotide, whereby said shortened at least partially double-stranded oligonucleotide is removed from the reaction mixture by immobilization to said support via the modification. In an alternative embodiment, upon formation of the ligation product the ligation product, said ligation product is immobilized to a support via the modification and the thus immobilized ligation product is cut by a type IIS restriction enzyme the recognition sequence of which is provided by the respective oligonucleotide library or any oligonucleotide which provides for a modification which allows the immobilization of the ligation product to a support, whereby the cutting provides for a plurality of elongated at least partially double-stranded oligonucleotides and shortened at least partially double-stranded oligonucleotide, whereby said shortened at least partially double-stranded oligonucleotide are bound or remain bound to the support.

Step 5 of the reaction consists of the removal of the shortened second at least partially double-stranded oligonucleotides which is preferably done by immobilization of the shortened second at least partially double-stranded oligonucleotide.

Due to this reaction sequence, the reaction and preferably the supernatant thereof contain a plurality of first elongated at least partially double-stranded oligonucleotides. In a further step, which is typically step 6, a second oligonucleotide library comprising several members is provided. Each member of such second oligonucleotide library is a third at least partially double-stranded oligonucleotide and comprises a double-stranded structure. The double-stranded structure may be designed such as outlined herein in connection with other at least partially double-stranded oligonucleotides such as the first at least partially double-stranded oligonucleotide. More specifically, the third oligonucleotide comprises a recognition site or part thereof, for a third type IIS restriction enzyme which cuts outside its recognition site, and a single-stranded overhang. The single-stranded overhang or part thereof is different for the members of the second oligonucleotide library. Such single-stranded overhangs or part thereof of the second oligonucleotide library are essentially complementary to the single-stranded overhangs of the elongated first at least partially double-stranded oligonucleotides. It will be understood by a person skilled in the art that due to the mechanism underlying the method of the present invention the overhang of one species of the plurality of the elongated first at least partially double-stranded oligonucleotides is complementary to one member of the second oligonucleotide library. It will also be acknowledged that the overhangs of the various species of the plurality of the elongated first at least partially double-stranded oligonucleotides and the overhang of the various members of the second oligonucleotide library, are, if taken in their entirety, complementary to each other, although not each overhang of the various first elongated at least partially double-stranded oligonucleotides will be complementary to each overhang of the member of the second oligonucleotide library. The second oligonucleotide library thus provides single-stranded overhangs of ATG, TAT and GAG, respectively. Accordingly, in the present case the second oligonucleotide library comprises three members. The members of the second oligonucleotide library further comprise a stretch of nucleotides in the double-stranded structure which is identical in all members and corresponds to the sequence or part thereof of the third or first stretch of nucleotides of the elements of the nucleotide acid library. The members of the second oligonucleotide library comprise a modification, whereby such modification is preferably the same as in connection with the first oligonucleotide library.

In step 7, the plurality of the first elongated at least partially double-stranded oligonucleotides and the second oligonucleotide library are combined. Due to the complementarity of the overhangs, one molecule of one species of the plurality of the first elongated at least partially double-stranded oligonucleotides is ligated with one molecule of one member of the second oligonucleotide library. The respective pair of molecules to be ligated is defined by the complementarity of the overhangs defining a reaction pair. Once the corresponding two oligonucleotides, as defined by their single-stranded overhangs, are hybridized or annealed, ligation typically occurs. The ligation product of such ligation reaction is called a second ligation product. In the present case, the second ligation product comprises a total of three different sequences and thus three different species, whereby the sequences of such species differ at least and typically exclusively in the sequence corresponding to the second stretch of the target sequence. The second ligation products form again a library.

The next steps, i.e. step 8 which is cutting the second ligation product with the third type IIS restriction enzyme, whereby the cleavage occurs in the nucleic acid sequence of the third at least partially double-stranded oligonucleotide is, in principle, designed the same way as described in connection with the first ligation product. This applies particularly with regard to the potential sequence of binding and cutting and removing by immobilization, respectively. As a result of step 8 in connection with which the second ligation product is cut with the third type IIS restriction enzyme a plurality of the second elongated at least partially double-stranded oligonucleotides which comprises a total of three different species of oligonucleotides, and shortened third at least partially double-stranded oligonucleotides is provided. Again, the shortened third at least partially double-stranded oligonucleotides thus released from the second ligation product are removed from the reaction by the modification and its interaction with an interaction partner such as streptavidin in connection with biotin being the modification bound to a surface.

In step 9 a fourth at least partially double-stranded oligonucleotide is provided. The fourth double-stranded oligonucleotide has a single-stranded overhang and otherwise the design of this fourth at least partially double-stranded oligonucleotide can be, in an embodiment, similar to the embodiments described in connection with other at least partially double-stranded oligonucleotides described in connection with FIG. 1(1) The single-stranded overhang of the fourth at least partially double-stranded oligonucleotide provides for a nucleotide sequence essentially complementary to the single-stranded overhang of the second elongated at least partially double-stranded oligonucleotide. The overhang of the second elongated at least partially double-stranded oligonucleotide is the same and thus identical for all of the three species of the second elongated at least partially double-stranded oligonucleotide as said overhang corresponds to the first triplet of the third stretch. Additionally, the fourth at least partially double-stranded oligonucleotide comprises a recognition site, or part thereof, for a fourth type IIS restriction enzyme which cuts outside its recognition site. The single-stranded overhang of such fourth at least partially double-stranded oligonucleotide is, as depicted in FIG. 1 (2), GAG and thus identical to the first triplet of the third stretch. Such fourth oligonucleotide and the plurality of the second elongated at least partially double-stranded oligonucleotides are combined and ligated. Again, one molecule of the fourth oligonucleotide is annealed to one molecule of second elongated at least partially double-stranded oligonucleotides due to the complementarity of the overhang of both oligonucleotides. The thus annealed molecules are then ligated providing a third ligation product. As in connection with other reactions, due to the complementarity of the overhangs, a one-on-one reaction, i.e. a reaction between one molecule of each species of reactant contained in the reaction, occurs. The third ligation product ultimately comprises the target sequence as depicted in FIG. 1 (1). Such third ligation product may be cut by the fourth type IIS restriction enzyme, whereby the cleavage occurs in the nucleic acid sequence of the fourth at least partially double-stranded oligonucleotide(s) and provides for a plurality of third elongated at least partially double-stranded oligonucleotides and shortened fourth at least partially double-stranded oligonucleotides. Again, the design of the sequence of further reactions may vary as outlined in connection with the first at least partially double-stranded oligonucleotide and the first oligonucleotide library.

As will be understood with regard to the sequences depicted specifically in FIG. 1(1), the type IIS restriction enzyme used for the cleavage is the one provided by the anchor molecules, i.e. those molecules which provide for the modification which allows the interaction with an interaction partner and thus immobilization of the molecule including any moiety which might have been added through ligation or removed by cleavage. The specific type IIS restriction enzyme inherent to all of the various anchor sequences used in connection with the example described in FIG. 1(1) is Eam1104I.

Such third elongated at least partially double-stranded oligonucleotide may be subject to further reaction steps which are also referred to as elongation steps as outlined above.

It will also be acknowledged by the persons skilled in the art that, alternatively, the thus obtained target sequence and more specifically the third elongated at least partially double-stranded oligonucleotide may then be used in a transposition step as described in connection with international patent application WO 00/75368.

Method for Preparing a Nucleic Acid Library as Illustrated in FIGS. 2(1), 2(2) and 2(3).

In connection with the method for the preparation of a nucleic acid library, whereby the elements thereof contain a variable position consisting of two subsequent nucleotide triplets, the following sequence of steps is typically applied. The target sequence as depicted in FIG. 2 (1) comprises as a first stretch CAC, as a second stretch which is variable in sequence and comprises in the instant example either (in 5'→3' direction) ATGCTC, ATGGAG, ATGTTT, TATGAG, TATCTC, TATTTT, GAGTTT, GAGCTC, or GAGGAG a nucleic acid sequence which is thus different for each element of the nucleic acid library, but in any case a sequence defined by a known nucleotide sequence rather than an arbitrary sequence, variable stretch and as a third stretch ACA.

The second variable stretch comprises in the illustrated case a first half of the second stretch and a second half of the second stretch, whereby the first half the second stretch exhibits one of the following triplets: ATG, TAT, or GAG, and the second half of the second stretch comprises the following different triplets: CTC, GAG, or TTT.

The particularity of this aspect of the method of the present invention is that the first half of the second stretch and the second half of the second stretch are provided or incorporated into the nucleic acid in different reaction steps. It will be acknowledged that the length of the first half of the second stretch and of the second half of the second stretch may vary, depending on the cutting characteristics of the type IIS restriction enzymes used. It is particularly preferred if the length of each of the first half and the second half consists of three consecutive nucleotides which code for an amino acid.

In a first step a first at least partially double-stranded oligonucleotide having a double-stranded structure is provided. Such at least partially double-stranded oligonucleotide has a single-stranded overhang and is also referred to herein as splinker. The single-stranded overhang provides for a nucleotide sequence corresponding to the sequence of the first or the third stretch of nucleotides or part thereof, of the elements of the nucleic acid library. More specifically, the single-stranded overhang sequence is complementary to said first or third stretch, respectively. In a preferred embodiment, the first at least partially double-stranded oligonucleotide comprises a recognition site or part thereof for a first type IIS restriction enzyme which cuts outside its recognition site. In the present case, such first at least partially double-stranded oligonucleotide has a single-stranded overhang comprising GTG and is thus complementary to the first triplet of the target sequence.

The at least partially double-stranded oligonucleotide in the embodiment depicted in FIG. 2 (1) is formed by a part of the single-stranded oligonucleotide folding back to another part of the oligonucleotide thus forming a loop and the double-stranded structure. However, it is also within the present invention that the at least partially double-stranded oligonucleotide is formed by two separate single-stranded oligonucleotides base-pairing to each other thus generating such at least partially double-stranded oligonucleotide also described herein. The end of the afore-described single-stranded oligonucleotide which is not providing the single-stranded overhang required for ligation is blocked so as to avoid any ligation or reaction as potentially possible in the subsequent steps of the method according to the present invention.

In step 2, a first oligonucleotide library is provided which comprises several members. Each member of said first oligonucleotide library is also referred to herein as a second at least partially double-stranded oligonucleotide and has a double-stranded structure. This kind of second at least partially double-stranded oligonucleotide is also referred to herein as anchor or anchor molecule. The double-stranded structure may, as in connection with the first at least partially double-stranded oligonucleotide, be formed by two single strands having the modification which allows for the immobilization of the second at least partially double-stranded oligonucleotides as described above, and particularly in connection with the embodiment depicted in FIG. 1(1). The members of the first oligonucleotide library comprise a recognition site, or part thereof, for a second type IIS restriction enzyme which cuts outside its recognition site. Furthermore, such second at least partially double-stranded oligonucleotide provides for a single-stranded overhang. The members of the first oligonucleotide library have a single-stranded overhang or part thereof which is the same for the members of the first oligonucleotide library and whereby such single-stranded overhang is essentially complementary to the single-stranded overhang of the first at least partially double-stranded oligonucleotide. In the present case, such single-stranded overhang is CAC. Subsequent to the single-stranded overhang, the double-stranded structure comprises a stretch of nucleotides and more specifically a double-stranded structure of double-stranded structure element, whereby the members of the first oligonucleotide library differ in the sequence of said stretch or double-stranded structure in the nucleotides and the sequences of said stretch of nucleotides corresponds to the sequences, or part thereof, of the first half of the second stretch of the nucleotides of the elements of the nucleic acid library according to the present invention. Accordingly, as depicted in FIG. 2 (1), a first oligonucleotide library is provided, whereby the members thereof, i.e. the second at least partially double-stranded oligonucleotides, are such characterized that the preferably double-stranded part of the members subsequent to the single-stranded overhang comprises the various sequences subject to the first half of the second stretch of the nucleotides of the elements of the nucleic acid library. In connection therewith, it is to be acknowledged that one member of the first oligonucleotide library comprises one of the respective possible sequences of the first half of the second stretch as also contained in one element, i.e. the corresponding element of the nucleic acid library. It is within the present invention that the double-stranded structure comprises further nucleotides which can, in an embodiment, or which cannot, in a different embodiment, contain further nucleotides of the target sequence. In the present case, the respective sequences are ATG, TAT and GAG which are base-pairing to the complementary sequences, i.e. (in 3'→5' direction) TAC, ATA and CTC forming part of the double-stranded structure of the second at least partially double-stranded oligonucleotides. The members of the first oligonucleotide library differ thus in the sequence of said stretch of nucleotides and the sequence of said stretch of nucleotides of the members of the first nucleotide library correspond to the sequence or part thereof of the first half of the second stretch of the nucleotides of the elements of the nucleic acid library.

Additionally, the members of the first oligonucleotide library comprise a modification, as described herein, which allows immobilising such molecules to or on a support which may be a carrier or surface comprising an interaction partner of said modification. Due to the presence of such modification, this kind of oligonucleotide is also referred to as anchor or anchor molecule. The immobilisation is specifically mediated by an interaction between the modification and an interaction partner of such modification. In the present case the modification is biotin which is interacting with streptavidin as its interaction partner and provides for a stable complex allowing the immobilisation of the members of the first oligonucleotide library. In FIG. 2(1) the recognition site for the type IIS restriction enzyme of the members of the first oligonucleotide library is indicated as a black box illustrating the fact that for this kind of restriction enzyme the recognition site is lying outside of the cleavage site. All of the members of the first oligonucleotide library have the same recognition site, or part thereof, for a type IIS restriction enzyme.

In step 3, the first at least partially double-stranded oligonucleotide and the first oligonucleotide library and the members thereof, respectively, are combined. Upon such combining, one molecule of the first at least partially double-stranded oligonucleotide is ligated to one molecule of one member of the first oligonucleotide library, preferably by means of a ligase or a ligase activity. Such ligation occurs upon forming a first pre-ligation product through the hybridisation of the single-stranded overhangs of the two kinds of molecules, with such overhangs acting as "sticky ends". The reaction product of the ligation is referred to as a first ligation product. Due to the complexity of the first oligonucleotide library which is in the instant case 3, also the first ligation products comprise 3 species which, at least, differ in the sequence corresponding to the first half of the second stretch. Typically the remainder of the first ligation products in terms of nucleotide sequences is preferably the same for the various elements and thus species of the thus formed first ligation product library.

In step 4, the first ligation product is cut with a type IIS restriction enzyme. Such type IIS restriction enzyme's recognition site is the one provided by the second at least partially double-stranded oligonucleotide, and is referred to herein as second type IIS restriction enzyme. The cutting of the first ligation product is performed on the pool and library, respectively, consisting of the first ligation products. Accordingly, the cutting or cleavage of the first ligation product results in a variety of thus cut molecules, whereby the reaction product of such cutting is a plurality of first elongated at least partially double-stranded oligonucleotides, and a plurality of shortened second at least partially double-stranded oligonucleotides. It will be acknowledged that the plurality of first elongated at least partially double-stranded oligonucleotides consists of various molecule species which differ in the sequence of the single-stranded overhang, It will also be acknowledged that the performance of step 3 and 4, respectively, can be carried out under different reaction conditions in terms of immobilizing or non-immobilizing the members of the first oligonucleotide library and the first ligation product, respectively. In each case, the respective molecules provide for a modification which, as outlined above, allows for the immobilization. Accordingly, any sequence with reference to the immobilization step can, in principle, be performed in various embodiments. Accordingly, it is within the present invention to perform the ligation reaction subject to step 3 in the liquid phase, i.e. with the members of the first oligonucleotide library not being immobilized. Subsequently, the cutting of the first ligation product occurs. In one embodiment, such cutting is then also performed in the liquid phase with the first ligation product not being immobilized to a support via its modification. After the cutting the shortened second at least partially double-stranded oligonucleotide is removed from the reaction mixture via its modification by binding to the support. Alternatively, after the ligation, the first ligation product can be immobilized to or on a support and the cutting step of the first ligation product is performed with the first ligation product being immobilized to such support. In any case, the shortened second at least partially double-stranded oligonucleotide is removed from the reaction by immobilizing it through its modification to a support. It will be acknowledged that due to the modification allowing a specific interaction such as between biotin and streptavidin, for immobilization purposes the reaction is transferred to a reaction vessel, preferably the walls of which have an interaction partner of the modification, in the present example given the modification being biotin, streptavidin. Due to the high affinity of biotin and streptavidin, the binding of the molecule containing the modification to the streptavidin comprising surface acting as support, occurs immediately. In other words, if a reaction is to be performed with a molecule having such modification, the reaction vessel or any support available in such reaction is not to comprise an interaction partner of the modification, whereas in case immobilisation is intended, a reaction vessel is used the surface of which provides for such interaction partner of the modification, either by the reaction vessel or by other surfaces or supports prevalent in such reaction.

Step 5 of the reaction consists of the removal of the shortened second at least partially double-stranded oligonucleotides which is preferably done by immobilization of the shortened second at least partially double-stranded oligonucleotide.

Due to this reaction sequence, the reaction and preferably the supernatant thereof contains a plurality of first elongated at least partially double-stranded oligonucleotides. The various first elongated at least partially double-stranded oligonucleotides define, by their single-stranded overhang, various species or subgroups of oligonucleotides. In the instant case, the plurality of first elongated at least partially double-stranded oligonucleotides comprises three different species or subgroups. Each subgroup in turn comprises various types of molecules which preferably differ with regard to the stretch of nucleotides forming the double-stranded stretch or part thereof and which corresponds to the second stretch of nucleotides, or part thereof, of the target nucleic acid. It will be acknowledged that the various subgroups preferably contain molecules which, in their entirety, have the same stretch of nucleotides forming the double-stranded stretch or part thereof and which corresponds to the second stretch of nucleotides, or part thereof, of the target nucleic acid. In a further step, which is typically step 6, a second oligonucleotide library comprising several members is provided. Each member of such second oligonucleotide library is a third at least partially double-stranded oligonucleotide and has a double-stranded structure. Said double-stranded structure may be designed such as outlined herein in connection with other at least partially double-stranded oligonucleotides such and preferably as the first at least partially double-stranded oligonucleotide. More specifically, the third at least partially double-stranded oligonucleotide comprises a recognition site or part thereof, for a third type IIS restriction enzyme which cuts outside its recognition site, and a single-stranded overhang. The single-stranded overhang or part thereof is different for the members of the second oligonucleotide library. In the present example, such overhang is either ATG, TAT or GAG. Such single-stranded overhangs or part thereof of the third at least partially double-stranded oligonucleotides are essentially complementary to the single-stranded overhang of the first elongated at least partially double-stranded oligonucleotides. It will be acknowledged by a person skilled in the art that only one species of the first elongated double-stranded oligonucleotides may be reacted and ultimately ligated with one species of the third at least partially double-stranded oligonucleotides, namely those the single-stranded overhangs of which are, preferably essentially or partially complementary to each other. Only taken in their entirety the overhangs of the various species of the first elongated at least partially double-stranded oligonucleotides and of the various species of the third at least partially double-stranded oligonucleotides are complementary to each other. The members of the second oligonucleotide library further comprise a stretch of nucleotides in the double-stranded structure which is different in the various members of the second oligonucleotide library. The diversity with regard to this stretch results from the combinatorial possibilities of the first half of the second stretch and the second half of the second stretch of the target sequence. In the instant example, the first half of the second stretch and the second half of the second stretch each comprise three different triplets so that the number of third at least partially double-stranded oligonucleotides must be 3×3, i.e. nine different molecules. If the first half consisted of three different triplets and the second half consisted of four different triplets, the complexity of the second oligonucleotide library would 3×4, i.e. 12 and said library would provide for 12 different species of oligonucleotides. Accordingly, in the instant case the second oligonucleotide library consists of 9 members thus providing any combination which arises from the variability of the second stretch of the target sequence, more specifically arising from the fact that such second stretch consists of a first and a second half contributing to the target sequence by different molecules whereby and each of such first and second stretch comprises three different forms or sequences resulting in the 9 different species. Again, the members of the second oligonucleotide library comprise a modification, whereby such modification is preferably the same as described in connection with the first oligonucleotide library.

In step 7, the plurality of the first elongated at least partially double-stranded oligonucleotides consisting of three different species, and the second oligonucleotide library are combined. Due to the complementarity of the overhangs as outlined above, each one molecule of the plurality, i.e. each one of the three different species of the first elongated at least partially double-stranded oligonucleotides is ligated with one molecule of a member of the second oligonucleotide library. The respective pair of molecules to be ligated is defined by the complementarity of their overhangs defining a reaction pair. Once the corresponding two molecules are hybridized or annealed, ligation typically occurs upon addition or presence of a respective ligase activity. In such ligation products, the first half of the second stretch and the second half of the second stretch of the target sequence is already contained in the ligation product and boxed in the representation of FIG. 2 (2). The nine different ligation products comprise, as a double-stranded stretch, already the first half of the second stretch of the target nucleic acid and the second half of the second stretch of the target nucleic acid.

In the present case, the second ligation product comprises a total of nine different sequences, whereby the sequences differ in the single-stranded overhang introduced into the second ligation product by the first elongated at least partially double-stranded oligonucleotides and, in the present example, the first triplet of the double-stranded structure provided by the members of the second oligonucleotide library. In other embodiments, further differences may reside in further parts of the ligation product, however, it is preferred that the two aforementioned differences in the various members of the library consisting of the second ligation product are otherwise the same. Again, the various members of the library consisting of the second ligation products have a type IIS restriction enzyme recognition site, or part thereof, which corresponds to the one of the second at least partially double-stranded oligonucleotides.

The next steps, i.e. the step 8, consists of the cutting of the second ligation product with the third type IIS restriction enzyme, whereby the cleavage occurs in the nucleic acid sequence of the third at least partially double-stranded oligonucleotide which is, in principle, designed and generated, respectively, the same way as described in connection with the first ligation product. This applies particularly with regard to the potential sequence of binding and cutting and removing by immobilization, respectively. As a result of step 8 in the course of which the second ligation product is cut with the third type IIS restriction enzyme, a plurality of second elongated at least partially double-stranded oligonucleotides and shortened third at least partially double-stranded oligonucleotides is provided. Again, the shortened third at least partially double-stranded oligonucleotides thus released from the second ligation product are removed from the reaction by the modification and its interaction with an interaction partner such as streptavidin in connection with biotin being the modification bound to a surface.

The thus obtained nine different second elongated at least partially double-stranded oligonucleotides are depicted in FIG. 2 (2).

In step 9 a third oligonucleotide library with a variety of fourth at least partially double-stranded oligonucleotides is provided. Said fourth at least partially double-stranded oligonucleotides differ in their overhangs. Otherwise, the design of this fourth at least partially double-stranded oligonucleotide can be, in an embodiment, similar to the embodiments described in connection with other at least partially double-stranded oligonucleotides described in connection with FIGS. 1(1) and 2(1) respectively. The single-stranded overhang provides for a nucleotide sequence which is essentially complementary to the single-stranded overhangs of the various second elongated at least partially double-stranded oligonucleotides. The number of the respective species of the third oligonucleotide library arises from and corresponds to the variability of the second half of the second stretch of the nucleic acid to be prepared, and thus the various second elongated at least partially double-stranded oligonucleotides. Such second elongated at least partially double-stranded oligonucleotides have, in the instant case, three different single-stranded overhangs, if taken together. More specifically, these overhangs are AAA, CTC, and GAG, being complementary to the second half of the second stretch of the target nucleic acid, namely TTT, GAG, and CTC. Additionally, the fourth at least partially double-stranded oligonucleotides comprise a recognition site, or part thereof, for a fourth type IIS restriction enzyme which cuts outside its recognition site. Such fourth at least partially double-stranded oligonucleotides, i.e. in the present example three different of these oligonucleotides, and the plurality of the second elongated at least partially double-stranded oligonucleotides, in the instant case nine different species of such oligonucleotides, are combined with each other and ligated by means of a ligase activity of the annealing of the two molecules by hybridisation through their complementary single-stranded overhangs. Again, on molecule of the fourth at least partially double-stranded oligonucleotides and one molecule of the various second elongated at least partially double-stranded oligonucleotides are annealed due to the complementarity of their overhangs. Insofar, one of said three different fourth at least partially double-stranded oligonucleotides is, in principle, reactive with three of the second elongated at least partially double-stranded oligonucleotides, namely those the single strand of which is complementary to the single strand of the respective fourth at least partially double-stranded oligonucleotide. This, again, gives a total of nine different oligonucleotides. The thus annealed molecules are then ligated by means of a ligase activity providing a third ligation product. Such third ligation product consists of nine different species of ligation products, whereby the ligation products contain both the first and the second half of the second stretch of the target nucleic acid, each of such sequences being flanked on both sides by another group, in the instant case three nucleotides. It will be acknowledged that the complexity of the libraries and oligonucleotides used in the method of the instant application immediately results from and corresponds to the variability of the first half and the second half of the second stretch of the nucleic acid to be prepared, or the multiplication product thereof. As in connection with other reactions, due to the complementarity of the overhangs, a one-on-one reaction, i.e. a reaction between one molecule of each species of reactant contained in the reaction, occurs. The third ligation product ultimately thus comprises the target sequence as depicted in FIG. 2 (1). The variable sequence of the target sequence, i.e. the one which is different in the various species of the ligation product, is boxed in FIG. 2 (3).

Again, as described in connection with the method of FIGS. 1(1) and 1(2), such molecule may be either cut with a type IIS restriction enzyme making use of the respective recognition sequence provided by the fourth at least partially double-stranded oligonucleotide, and be subject to further reactions using the same reaction schemes as outlined above, or it may be subject to the cleaving using a type IIS restriction enzyme which is then provided by the third at least partially double-stranded oligonucleotide allowing to release the target sequence. In the latter alternative, the third ligation product may thus be cut so as to be introduced in a transposition reaction with other molecules, typically prepared in a similar manner so as to allow a transposition reaction as described in connection with WO 00/75368.

Method for Preparing a Nucleic Acid Library as Illustrated in FIGS. 3(1) and 3(2).

In a further alternative of the methods according to the present invention and more specifically the method according to the first aspect, a target sequence is to be synthesised as depicted in FIG. 3 (1), whereby the first position, i.e. the first triplet in the case depicted, is variable and in the instant case consists of three nucleotides. Such variable position is also referred to as the first stretch, whereas the subsequent triplets are referred to as the second and the third stretch, respectively. Except the issues discussed in the following, the steps and the molecules used in such method correspond to the ones described herein in connection with the method according to the first aspect of the present invention which are incorporated herein by reference in order to avoid any unnecessary repetition.

In a first step, a plurality of first at least partially double-stranded oligonucleotides is provided. Such at least partially double-stranded oligonucleotides have a double-stranded structure and a single-stranded overhang. This kind of molecules is also referred to herein as splinker. These first at least partially double-stranded oligonucleotides differ with regard to the sequence of the single-stranded overhang. The diversity of the single-stranded overhangs corresponds to the diversity of the variable position, whereby the overhangs of the various species of the first at least partially double-stranded oligonucleotides are complementary to the sequences of the various elements of the nucleic acid library to be prepared and thus complementary to the first stretch. In the instant example, the overhang is either (in 3'→5' direction) TAC, ATA, or CTC. In an embodiment, the first at least partially double-stranded oligonucleotides comprise a recognition site, or part thereof, for a first type IIS restriction enzyme which cuts outside its recognition site.

In a second step a first oligonucleotide library is provided which comprises several members and several species, respectively. Each member of said first oligonucleotide library is also referred to herein as a second at least partially double-stranded oligonucleotide and has a double-stranded structure. The double-stranded structure may, as in connection with the first at least partially double-stranded oligonucleotide, be formed by two single strands having a further modification as described above which, in principle, allows the immobilisation of such first oligonucleotide library on a support, whereby such support comprises or provides for an interaction partner to such modification. In a preferred example, the modification is biotin and the interaction partner of such support is streptavidin. The members of the first oligonucleotide library comprise a recognition site, or part thereof, for a second type IIS restriction enzyme which cuts outside its recognition site. Furthermore, such second at least partially double-stranded oligonucleotides provide for a single-stranded overhang. The members and species, respectively, of the first oligonucleotide library differ insofar from each other that the single-stranded overhang or part thereof is different for the members or species of the first oligonucleotide library and whereby such single-stranded overhangs are essentially or partially complementary to the single-stranded overhang of the first at least partially double-stranded oligonucleotides. In the present case, such single-stranded overhangs are ATG, TAT and GAG, respectively. Again, the complexity of the library is defined by the variability of the first stretch of the nucleic acid to be prepared. Accordingly, if the complexity was, as depicted in the example, three because of the three different sequences, the plurality of the first at least partially double-stranded oligonucleotides and of the first oligonucleotide library will be three. Subsequent to the single-stranded overhang, the double-stranded structure of the second at least partially double-stranded oligonucleotides comprise a stretch of nucleotides, whereby the members of the first oligonucleotide library have the same sequence. Immediately following the three nucleotides comprising overhang, the second at least partially double-stranded oligonucleotides have a stretch which corresponds to the sequence of the second stretch of the target sequence. In the second at least partially double-stranded oligonucleotides, however, such second stretch of the target sequence is present in a double-stranded form. The plurality of the first at least partially double-stranded oligonucleotides and the first oligonucleotide library and its members, i.e. the second at least partially double-stranded oligonucleotides, are depicted in FIG. 3(1).

The members of the first oligonucleotide library comprise a modification. In the present case, such modification allows the immobilisation of the various members of the library to a support which is typically the surface of a reaction tube or of a well. The immobilisation is specifically mediated by an interaction by the modification and the interaction partner of such modification which is typically present on the support or carrier. In the present case, the modification is biotin which is interacting with streptavidin as its interaction partner provides for a stable complex allowing the immobilisation of the members of the first oligonucleotide library.

As in connection with the methods depicted in FIGS. 1 and 2, the recognition site for the type IIS restriction enzyme of the members of the first oligonucleotide library is indicated as a black box illustrating the fact that for this kind of restriction enzyme the recognition site is lying outside of the cleavage site.

In step 3, the first at least partially double-stranded oligonucleotides and the members of the first oligonucleotide library are combined. Upon such combining, one molecule of the first at least partially double-stranded oligonucleotide is ligated to one molecule of the members of the first oligonucleotide library, preferably by means of a ligase or ligase activity. Such ligation occurs forming a first pre-ligation product through the hybridisation of the single-stranded overhangs of the two kinds of molecules with such overhangs acting as "sticky ends". The reaction product of the ligation is referred to, in their entirety, as a first ligation product as depicted in FIG. 3 (1). As indicated in FIG. 3 (1) such first ligation product varies and represents the variable positions of the target sequence. In other words, the first ligation product forms a library itself which comprises, in the instant example, three different species of ligation product which differ at the position representing the variable position of the target sequence. Such ligation product additionally comprises the second stretch of the target sequence which is, in the present case, GAG. Insofar, the members of this pool of ligation products at least and preferably differ only in the sequence corresponding to the first triplet of the target sequence which is the variable position, whereas typically the remainder of the first ligation product in terms of nucleotide sequence is preferably the same for the various elements of the thus formed first ligation product library.

In step 4, the first ligation product is cut with a type IIS restriction enzyme. Such type IIS restriction enzyme is the one the recognition site of which is provided by the anchor molecules, i.e. by the second at least partially double-stranded oligonucleotides. The cutting of the first ligation products is performed on the pool and library, respectively, consisting of the first ligation products. Accordingly, the cutting or cleavage of the first ligation products results in a variety of thus cut molecules, whereby the reaction product of such cutting is a plurality of first elongated at least partially double-stranded oligonucleotides, and a plurality of shortened second at least partially double-stranded oligonucleotides. In each case, in the present example, there a three different species of the respective molecules provided As described in connection with the methods subject to FIGS. 1 and 2, the performance of step 4 can be carried out under the different scenarios in terms of immobilisation or non-immobilisation of the members of the first ligation product, respectively. The respective disclosure is incorporated herein by reference.

The further step of the reaction consists in the removal of the shortened second at least partially double-stranded oligonucleotides which is preferably done by immobilisation of the shortened second at least partially double-stranded oligonucleotides.

Due to the reaction scheme, the reaction, preferably the supernatant thereof, contains a plurality of at least partially double-stranded oligonucleotides which are also referred to as first elongated at least partially double-stranded oligonucleotides. Such plurality of oligonucleotides consists of three different species which have the same sequence in the single-stranded overhang, but differ in the sequence of the adjacent three nucleotides which correspond to the target sequence and which is boxed in FIG. 3(2). In a further step, which is typically step 6, a third at least partially double-stranded oligonucleotide is provided. The third at least partially double-stranded oligonucleotide has a double-stranded structure which may be designed such as outlined herein in connection with other at least partially double-stranded oligonucleotides and preferably as the first at least partially double-stranded oligonucleotide. More specifically, such third at least partially double-stranded oligonucleotide comprises a recognition site or part thereof for a third type IIS restriction enzyme which cuts outside its recognition site, and the single-stranded overhang. The single-stranded overhang or part thereof is complementary to the single-stranded overhang of the elongated first at least partially double-stranded oligonucleotides. Because of this the third at least partially double-stranded oligonucleotide consists of one species only. The third at least partially double-stranded oligonucleotide thus comprises a stretch of nucleotides in the double-stranded structure which is identical to the third stretch of the target sequence, i.e. in the present case ACA. This third at least partially double-stranded oligonucleotide, which, due to having a modification, allows its immobilisation as described above and which may also thus be referred to as anchor molecule, is then ligated to the three members of the library forming the plurality of first elongated at least partially double-stranded oligonucleotides. Again, the annealing and ligation is performed in a way similar to the one described in connection with other ligation procedures. Additionally, such ligation procedures may be varied in accordance with what has been said above. In other words, due to the complementarity of the overhangs, each molecules of the plurality of first elongated at least partially double-stranded oligonucleotide is ligated with a single molecule of the third at least partially double-stranded oligonucleotide. The thus formed ligation product of such ligation reaction is also referred to as second ligation product and depicted in FIG. 3 (2) with the variable stretch of the target sequence being boxed. Such ligation product comprises then the overall target sequence, whereby the first position thereof shows the variability of the target sequence, represented by the different species of the second ligation product.

Method for Preparing a Nucleic Acid Library as Illustrated in FIGS. 4(1), 4(2) and 4(3).

In another embodiment of the method according to the present invention and more specifically of the second aspect thereof, the target sequence is as depicted in FIG. 4 (1), i.e. comprises two variable positions forming a first stretch, more specifically a first half of the first stretch and a second half of the first stretch, and a second stretch. Except the issues discussed in the following, the steps and the molecules used in such method correspond to the ones described herein in connection with the method according to the second aspect of the present invention which are incorporated herein by reference in order to avoid any unnecessary repetition.

In the instant example, the first half of the first stretch consists of one of the three triplets ATG, TAT and GAG, and the second half of the first stretch consists of either CTC, GAG or TTT. The second stretch consists of ACA.

In a first step, a plurality of first at least partially double-stranded oligonucleotides is provided. Such plurality of first at least partially double-stranded oligonucleotides shown in FIG. 4(1) comprises three different species of first at least partially double-stranded oligonucleotides. The different species or members of this kind of library differ at least and preferably in the single-stranded overhang. The various first at least partially double-stranded oligonucleotides differ more specifically such that the single-stranded overhang is (in 3'→5' direction) TAC, ATA, and CTC thus being complementary to the various sequences of the variable sequence of the first half of the first stretch of the target sequence. Apart from that, this kind of first at least partially double-stranded oligonucleotides has a structure similar or identical to the one described in connection with the other embodiments of the method of the present invention, and more specifically those of the second aspect of the methods according to the present invention, more particularly comprise a recognition sequence or part thereof of a first type IIS restriction enzyme.

In step 2, a first oligonucleotide library is provided which comprises several members. Each member of said first oligonucleotide library is also referred to herein as a second at least partially double-stranded oligonucleotide and has a double-stranded structure. The double-stranded structure may, as in connection with the first at least partially double-stranded oligonucleotide be formed by two single strands having the further modification as described above. The members of the first oligonucleotide library comprise a recognition site, or part thereof, for a second type IIS restriction enzyme which cuts outside its recognition site. Furthermore, such second at least partially double-stranded oligonucleotide provides for a single-stranded overhang. The members of the first oligonucleotide library differ at least insofar from each other that the single-stranded overhang or part thereof is the same for a subgroup of the members of the first oligonucleotide library and whereby such single-stranded overhang is essentially or partially complementary to the single-stranded overhang of one species of the various first at least partially double-stranded oligonucleotides. In other words, the complexity of the first library is determined by the complexity of the nucleic acid library to be prepared and may be calculated by multiplying variability of the first half of the first stretch with the variability of the second half of the first stretch. Accordingly, in their entirety, all of the oligonucleotides of the plurality of the first at least partially double-stranded nucleic oligonucleotides have an overhang which, again in their entirety, will be complementary to the overhangs of the oligonucleotides of the first oligonucleotide library. More specifically, such single-stranded overhang is either ATG, corresponding to the single-stranded overhang of the first at least partially double-stranded oligonucleotide TAC, TAT, corresponding to the single-stranded overhang of the first at least partially double-stranded oligonucleotide ATA, and GAG corresponding to the single-stranded overhang of the first at least partially double-stranded oligonucleotide CTC. Insofar, this first oligonucleotide library provides three different species in terms of different overhangs. Each of this species comprises three further species which are characterised insofar that immediately following the single-stranded overhangs, the sequence in accordance with the second half of the first stretch of the target sequence is repeated. Such sequence of nucleotides is part of the double-stranded structure. Insofar, the first subgroup of the first oligonucleotide library consists of ATG CTG/GAG, ATG GAG/CTC and ATG TTT/AAA, the second sub-species consists of TAT CTC/GAG, TAT GAG/CTC and TAT TTT/AAA, the third sub-species consists of GAG CTC/GAG, GAG GAG/CTC and GAG TTT/AAA, whereby the nucleotides indicated after the "/" are indicative for the three nucleotides being complementary to the immediately proceeding three nucleotides. Insofar, the first oligonucleotide library consists of nine members which are formed by the variability of the first half of the first stretch multiplied with the variants of the second half of the first stretch. In other words, the number of the members of the first oligonucleotide library is the product of the number of different sequences of the first half of the first stretch multiplied with the number of different sequences of the second half of the first stretch of the target nucleic acid.

Similar to the members of the first oligonucleotide libraries used in connection with the other embodiments of the instant invention, the second at least partially double-stranded oligonucleotides comprise a modification as specified in connection therewith.

In step 3, the various first at least partially double-stranded oligonucleotides and the first oligonucleotide library and the members thereof, respectively, are combined. Upon such combining, one molecule of the first at least partially double-stranded oligonucleotide is ligated to one molecule of one member of the first oligonucleotide library, preferably by means of a ligase or ligase activity. Such ligation occurs upon forming a first pre-ligation product through the hybridisation of the corresponding single-stranded overhangs of the two kinds of molecules with such overhangs acting as sticky ends. The reaction product of the ligation is referred to as a first ligation product. Due to the variety of the first at least partially double-stranded oligonucleotide and the first oligonucleotide library the ligation reaction results in a pool of first ligation products, in the present case of nine different species of such first ligation products. Such ligation products differ in their sequence insofar that they contain the variable second stretch consisting of the first half and the second half of the first stretch of the target nucleic acid which is indicated as a box in FIG. 4 (2). Apart from this, the ligation products which actually constitute a further library differ insofar and preferably in this sequence, whereas typically the remainder of the first ligation product in terms of nucleotide sequence is preferably the same for the various elements of the thus formed first ligation product library.

In step 4, the various first ligation products are cut with a type IIS restriction enzyme. Such type IIS restriction is the one the recognition site of which is the one provided by the second at least partially double-stranded oligonucleotides (which is marked by a black box in FIGS. 4(1,2). The cutting of the first ligation product is performed on the reaction and library, respectively, comprising the first ligation product(s). Accordingly, the cutting or cleavage of the first ligation product results in a variety of thus cut molecules, whereby the reaction product of such cutting is a plurality of first elongated at least partially double-stranded oligonucleotides and a plurality of shortened second at least partially double-stranded oligonucleotides. As in the various other embodiments described in connection with FIGS. 1 to 3, such second type IIS restriction enzyme is Eam1104I.

Again, it will be acknowledged that the performance of step 4 can be carried out under different scenarios in terms of immobilisation or non-immobilisation of the members of the first oligonucleotide library as described in connection with the other embodiments of the method according to the invention.

Due to the cutting of the first ligation product a total of nine different first elongated at least partially double-stranded oligonucleotides is generated. Typically, the individual species of the thus generated plurality or variety of first elongated at least partially double-stranded oligonucleotides comprises nine different species defined by the various intended target sequences, whereby three different subgroups of molecules exist which are defined by their single-stranded overhang which are complementary to the second half of the first stretch of the target sequence. More specifically, in the instant example, the three subgroups are those which are defined by a single-stranded overhang of GAG, one defined by a single-stranded overhang of CTC and one defined by a single-stranded overhang of AAA. Each subgroup in turn varies insofar that the stretch and in particular the three nucleotides following or preceding, respectively, the single-stranded overhang and which form the first double-stranded stretch of the double-stranded structure, correspond to the first half of the first stretch of the target sequence and, thus, are ATG/TAC, TAT/ATA, and GAG/CTC, respectively, for each of said subgroups.

In a next step a second oligonucleotide library consisting of third at least partially double-stranded oligonucleotides is added as depicted in FIG. 4 (2). The members of the second oligonucleotide library differ with regard to their single-stranded overhangs which correspond to the second half of the first stretch of the target sequence, i.e. in the present case CTC, GAG, and TTT. Otherwise, the members are the same as described in connection with the first oligonucleotide library, whereby they comprise a recognition sequence for a third type IIS restriction enzyme, or part thereof, and comprise a modification.

The first part of the double-stranded structure of the third at least partially double-stranded oligonucleotide following the single-stranded overhang is the same within all of the members of the second oligonucleotide library and corresponds to the second stretch of the target sequence, which is in the present case ACA. As this stretch of the third at least partially double-stranded oligonucleotide is part of the double-stranded structure of such third at least partially double-stranded oligonucleotide the respective double-stranded structure in the various members of the second oligonucleotide library is thus ACA/TGT for each and any of the members of such second oligonucleotide library.

The members of the second oligonucleotide library are then ligated, typically after an annealing step, with the various first elongated at least partially double-stranded oligonucleotides and insofar, the further steps correspond to the one described in connection with each and any of the other embodiments of the method according to the instant invention. The respective reaction product is the second ligation product which consists, as determined by the complexity of the nucleic acid library to be prepared, of nine different species.

It will be understood by the persons skilled in the art, that it is possible to vary the concentration with which the various at least partially double-stranded oligonucleotides are added to the individual reactions. Apart from any equimolar ratio relative to each other, the ratio may be biased which will result in an over- or under-representation of the variable position introduced into the nucleic acid molecule by the respective oligonucleotide(s). In accordance therewith the nucleic acid library prepared by the methods according to the instant invention reflects in terms of prevalence of the various elements the biased ratio of the at least partially double-stranded oligonucleotides used as anchor molecules.

It will be acknowledged that the methods according to the present invention may be used for the preparation of a single-stranded nucleic acids as well as double-stranded nucleic acids. The preparation of a single-stranded nucleic acid is typically based on the preparation of a double-stranded nucleic acid, whereupon the double-stranded nucleic acid is denaturated providing for the respective single-stranded nucleic acids. The separation of the two single strands may be effected in case the various oligonucleotides used in the preparation of the double-stranded nucleic acid, each consist of two single strands which are not covalently linked to each other. Alternatively, the covalently linked single strands providing for the double-strands may be separated by covalent cleavage.

It will also be acknowledged that the methods according to the present invention may be used for the preparation of a nucleic acid library, whereby the elements of the nucleic acid library differ in the sequence, particularly in the second stretch, and whereby such stretch consists of more than six nucleotides as illustrated herein. As a matter of fact, the repetition of the individual steps, i.e. repeating steps n) to q) as steps na) to qa), whereby the fifth at least partially double-stranded oligonucleotide of step n) is a further at least double-stranded oligonucleotide in step na), the fourth ligation product in step o) is a further ligation product in step oa), the plurality of fourth elongated at least partially double-stranded oligonucleotides in step p is a plurality of further elongated at least partially double-stranded oligonucleotides in step pa), and the shortened fifth at least partially double-stranded oligonucleotide of step p) is a shortened further at least double-stranded oligonucleotide in step pa), is not limiting the number of the nucleotides which are different in the various elements of the nucleic acid library. Rather the methods according to the present invention allow the preparation of stretches significantly longer, depending on the purpose for which the nucleic acid library is prepared. In case of providing an optimized active centre of an enzyme or an antibody having an optimized binding site, the length of the stretch which is different in the various members of the nucleic acid library, corresponds to the length of the amino acid sequence which form the active centre of such enzyme or the binding site of such antibody, and the nucleic acid coding therefore, respectively.

Finally, it will be acknowledged that the length of the second stretch of nucleotides of the elements of the nucleic acid library, or any stretch of nucleotides corresponding thereto, preferably corresponding thereto in terms of function, may consist, in principle of any length. Preferably, it consists of two nucleotides, three nucleotides, four nucleotides, five nucleotides, six nucleotides, seven nucleotides or eight or multiples of three nucleotides.

EXAMPLE 1

Manufacture of a Nucleic Acid Library with a Single Variable Position

As outlined above, the invention provides a highly efficient method for the synthesis of a nucleic acid library. An example for the generation of a library with a single variable position as also depicted in FIG. 1(1) is described in more detail in the following. The variable position covers 20 different codons (rather than three as depicted in the figures) representing all possible amino acids, the codon usage was adapted to E. coli.
1) First Ligation
20-200 pmol of a Splinker molecule, i.e. a first at least partially double-stranded oligonucleotide, with a GTG overhang were provided in a reaction vessel in 25 to 200 μl reaction buffer. Then, 20-200 pmol of a mixture of 20 Anchor molecules, i.e. the first oligonucleotide library, were added. These Anchors are present in the mixture in equimolar amounts and all have the same single-stranded overhang (CAC, corresponding to the first stretch) that is complementary to the overhang of the Splinker molecule but they differ in their adjacent variable part representing the codons for the 20 different amino acids (see table 1). After addition of 10 to 50 U T4-DNA-Ligase the molecules were ligated for 60 minutes at 25° C. providing a plurality of first ligation products.
2) Isolation of a Plurality of First Elongated at Least Partially Double-Stranded Oligonucleotides
The plurality of first ligation products was immobilized via its biotin moiety to a streptavidin-coated vessel or well for 15 minutes at room temperature. Unbound material was removed by washing three times with wash buffer (33 mM Tris/Acetate, 10 mM Magnesium Acetate, 66 mM, Potassium Acetate, pH 7.9). Then, 10 to 100 U of a restriction enzyme such as Eam1104I which is the second type IIS restriction enzyme were added in 25 to 200 μl reaction buffer followed by an incubation of 15 to 90 minutes at 37° C. The plurality of first elongated at least partially double-stranded oligonucleotides thus released was transferred to a new vessel or well.
3) Second Ligation
20-200 pmol of a mixture of 20 Anchor molecules, i.e. a second oligonucleotide library, were added to the plurality of first elongated at least partially double-stranded oligonucleotides in 25 to 200 μl reaction buffer. The Anchor molecules are present in the mixture in equimolar amounts and differ in their single-stranded overhangs (corresponding to the second stretch of the target sequence) that are complementary to the overhangs provided by the plurality of first elongated oligonucleotides but are all identical in their adjacent part. After addition of 10 to 50 U T4-DNA-Ligase the molecules were ligated for 60 minutes at 25° C. providing a plurality of second ligation products.
4) Isolation of a Plurality of Second Elongated at Least Partially Double-Stranded Oligonucleotides
The plurality of second ligation products was immobilized via its biotin moiety to a streptavidin-coated vessel or well for 15 minutes at room temperature. Unbound material was removed by washing three times with wash buffer. Then, 10 to 100 U of a restriction enzyme such as Eam1104I which is the second type IIS restriction enzyme were added in 25 to 200 μl reaction buffer followed by an incubation of 15 to 90 minutes at 37° C. The plurality of second elongated at least partially double-stranded oligonucleotides thus released was transferred to a new vessel or well.
5) Third Ligation
20-200 pmol of an Anchor molecule, i.e. a fourth at least partially double-stranded oligonucleotide, with an overhang (GAG, corresponding to the first half of the third stretch) that is complementary to the overhang provided by the plurality of second elongated at least partially double-stranded oligonucleotides (CTC) was added to the plurality of second elongated at least partially double-stranded oligonucleotides in 25 to 200 μl reaction buffer. After addition of 10 to 50 U T4-DNA-Ligase the molecules were ligated for 60 minutes at 25° C. providing a plurality of third ligation products.
6) Synthesis of an Elongation Block
An elongation cycle comprising binding of the third ligation product to the streptavidin surface, cleaving of the immobilized product by Eam1104I and ligation of the thus released elongated oligonucleotides with an appropriate Anchor was repeated three times starting from the third ligation product of step 5, resulting in a plurality of sixth ligation products, also referred to as elongation blocks. The conditions of each reaction step were as described above.

7) Synthesis of the Final Product

The elongation block thus synthesized was used in the subsequent synthesis of the complete gene product via the transposition method described earlier (international patent application WO 00/75368)

8) Quality Assessment of the Final Product

The final product, i.e. a nucleic acid library having a single variable position was cloned into a standard vector (pPCR-Script, Stratagene) and 96 single clones were sequenced. The sequences of the elements of the desired nucleic acid library appeared to be identical except from their particular variable position. The obtained distribution of the 20 different codons at the variable position is shown in Table 1.

TABLE 1

| Overhang | Amino Acid | No. of sequences |
| --- | --- | --- |
| Total | | 96 |
| GAA | E | 3 |
| ATT | I | 3 |
| CTT | L | 7 |
| GTG | V | 3 |
| TTT | F | 7 |
| ATG | M | 1 |
| TGC | C | 7 |
| GCA | A | 9 |
| GGC | G | 2 |
| CCT | P | 9 |
| ACA | T | 3 |
| AGC | S | 3 |
| TAT | Y | 7 |
| TGG | W | 6 |
| CAA | Q | 7 |
| AAC | N | 4 |
| GAT | D | 4 |
| CAT | H | 5 |
| AAG | K | 1 |
| AGA | R | 5 |

Figure 5:
FIG. 5 is a histogram indicating the codon frequencies obtained in the synthesis of a nucleic acid library using the method according to the first aspect of the instant application.

The respective figures together with the statistical analysis thereof are indicated in FIG. 5 which is a histogram of obtained codon frequencies at a single permutated position. The expected value $\mu$ of each of the 20 codons in a sample of 96 is 4.8, if equal distribution is assumed. In this case it is expected that more than 95% of all codons lie within a range of two standard deviations ($\mu+/-2\sigma$). In this example, all observed frequencies are well within a range of 2 standard deviations of a normal distribution, supporting the hypothesis of an equal distribution of codon frequencies.

EXAMPLE 2

Manufacture of a Nucleic Acid Library with a Stretch of Variable Positions

Example 2 is an example for the generation of a library with a stretch of two variable positions each comprising three subsequent nucleotides forming a triplet coding for an amino acid as also depicted in FIG. 2(1) and is described in more detail in the following. The variable positions contain 10 different codons each giving a complexity of the library of 100 (10×10) rather than three different codons as illustrated in FIG. 2(1) The codon usage was adapted to E. coli.

1) First Ligation 20-200 pmol of a Splinker molecule, i.e. a first at least partially double-stranded oligonucleotide, with a GTG overhang were provided in a reaction vessel in 25 to 200 µl reaction buffer. Then, 20-200 pmol of a mixture of 10 Anchor molecules, i.e. the first oligonucleotide library, were added. These Anchors are present in the mixture in equimolar amounts and all have the same single-stranded overhang (CAC, corresponding to the first stretch of the target sequence) that is complementary to the overhang of the Splinker molecule but they differ in their adjacent variable part representing the codons for 10 different amino acids (see table 2). After addition of 10 to 50 U T4-DNA-Ligase the molecules were ligated for 60 minutes at 25° C. providing a plurality of first ligation products.

2) Isolation of a Plurality of First Elongated at Least Partially Double-Stranded Oligonucleotides The plurality of first ligation products was immobilized via its biotin moiety to a streptavidin-coated vessel or well for 15 minutes at room temperature. Unbound material was removed by washing three times with wash buffer (33 mM Tris/Acetate, 10 mM Magnesium Acetate, 66 mM, Potassium Acetate, pH 7.9). Then, 10 to 100 U of a restriction enzyme such as Eam1104I which is the second type IIS restriction enzyme were added in 25 to 200 µl reaction buffer followed by an incubation of 15 to 90 minutes at 37° C. The plurality of first elongated at least partially double-stranded oligonucleotides thus released was transferred to a new vessel or well.

3) Second Ligation 20-200 pmol of a mixture of 100 different Anchor molecules (10 triplets as of the first half of the second stretch multiplied with 10 triplets as of the second half of the second stretch, whereby the second stretch is the stretch of the nucleic acid library to be prepared which provides the variable positions), i.e. the second oligonucleotide library, were added to the plurality of the first elongated at least partially double-stranded oligonucleotides in 25 to 200 µl reaction buffer. All Anchor molecules are present in the mixture in equimolar amounts and differ in their single-stranded overhangs (corresponding to the first half of the second stretch of the target sequence) that are complementary to the 10 different overhangs provided by the plurality of first elongated oligonucleotides as well as in their adjacent part. In the adjacent part also 10 different codons were provided leading to a combinatorial mixture of 100 Anchors. After addition of 10 to 50 U T4-DNA-Ligase the molecules were ligated for 60 minutes at 25° C. providing a plurality of second ligation products.

4) Isolation of a Plurality of Second Elongated at Least Partially Double-Stranded Oligonucleotides The plurality of second ligation products was immobilized via its biotin moiety to a streptavidin-coated vessel or well for 15 minutes at room temperature. Unbound material was removed by washing three times with wash buffer. Then, 10 to 100 U of a restriction enzyme such as Eam1104I which is the second type IIS restriction enzyme were added in 25 to 200 µl reaction buffer followed by an incubation of 15 to 90 minutes at 37° C. The plurality of second elongated at least partially double-stranded oligonucleotides thus released was transferred to a new vessel or well.

5) Third Ligation 20-200 pmol of a mixture of 10 Anchor molecules, i.e. the third oligonucleotide library, was added to the plurality of second elongated at least partially double-stranded oligonucleotides in 25 to 200 µl reaction buffer. The Anchor molecules are present in the mixture in equimolar amounts and differ in their single-stranded overhangs (corresponding to the second half of the second stretch of the target sequence) that are complementary to the overhangs provided by the plurality of first elongated oligonucleotides but are all identical in their adjacent part constituting the third stretch of the target sequence. After addition of 10 to 50 U T4-DNA-Ligase the molecules were ligated for 60 minutes at 25° C. providing a third ligation product which actually consists of a plurality of third ligation products.

6) Isolation of a Plurality of Second Elongated at Least Partially Double-Stranded Oligonucleotides The plurality of third ligation products was immobilized via its biotin residue to a streptavidin-coated vessel or well for 15 minutes at room temperature. Unbound material was removed by washing three times with wash buffer. Then, 10 to 100 U of a restriction enzyme such as Eam1104I which is the second type IIS restriction enzyme were added in 25 to 200 µl reaction buffer followed by an incubation of 15 to 90 minutes at 37° C. The plurality of third elongated at least partially double-stranded oligonucleotides thus released was transferred to a new vessel or well.

7) Fourth Ligation 20-200 pmol of an Anchor molecule, i.e. the fifth at least partially double-stranded oligonucleotide, with an overhang (ACA, corresponding to the third stretch of the target sequence) that is complementary to the overhang provided by the plurality of third elongated at least partially double-stranded oligonucleotides (TGT) was added to the plurality of third elongated at least partially double-stranded oligonucleotides in 25 to 200 µl reaction buffer. After addition of 10 to 50 U T4-DNA-Ligase the molecules were ligated for 60 minutes at 25° C. providing a fourth ligation product which actually consists of a plurality of fourth ligation products.

8) Synthesis of an Elongation Block

This elongation cycle comprising binding of the ligation product to the streptavidin surface, cleaving of the immobilized product by Eam1104I and ligation of the thus released elongated oligonucleotides with an appropriate Anchor was repeated two times resulting in a plurality of sixth ligation products, also referred to as elongation blocks. The conditions of each reaction step were as described above.

9) Synthesis of the Final Product

The elongation block thus synthesized was used in the subsequent synthesis of the complete gene product via the transposition method described earlier (international patent application WO 00/75368)

10) Quality Assessment of the Final Product

The final product, i.e. a nucleic acid library having a variable stretch comprising of two triplets, whereby each triplet is coding for one out of a total of 10 possible amino acids at the respective position, was cloned into a standard vector and 62 single clones were sequenced. The sequences appeared to be identical except from their particular two variable positions. The obtained distribution of the 10 different codons at the variable positions is shown in Table 2.

TABLE 2

| Triplets | Variable Triplet 1 | Variable Triplet 2 |
|---|---|---|
| AAA | 3 | 5 |
| ATG | 9 | 5 |
| ACT | 8 | 5 |
| CCC | 6 | 7 |
| CCG | 10 | 7 |
| CTG | 9 | 10 |
| GAT | 7 | 2 |
| GCA | 4 | 7 |
| TTA | 4 | 7 |
| TGG | 2 | 7 |
| Total | 62 | 62 |

Figure 6:
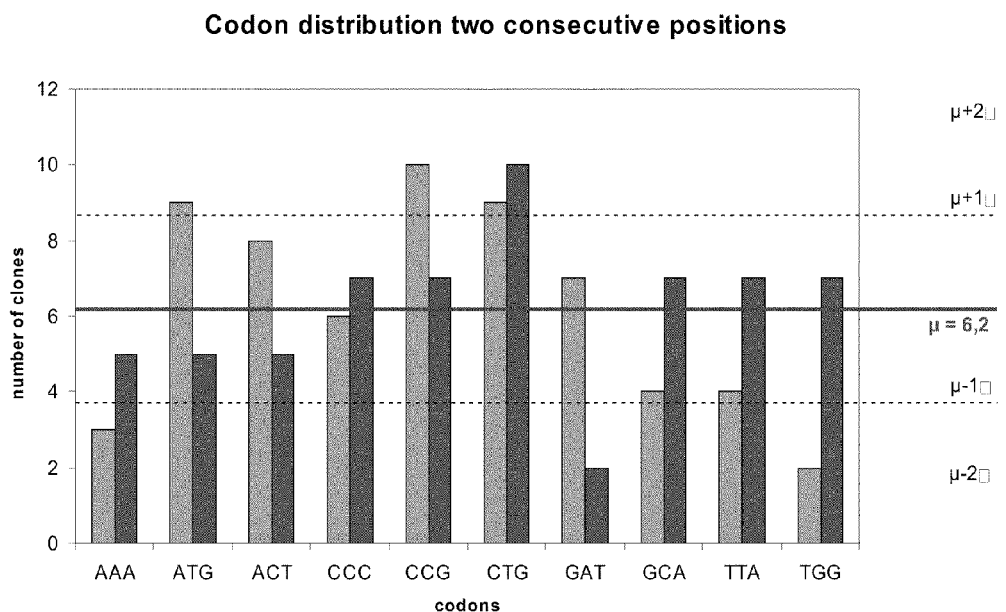
FIG. 6 is a histogram indicating the codon frequencies at two consecutive positions obtained in the synthesis of a nucleic acid library using the method according to the second aspect of the instant application.

The respective figures together with the statistical analysis thereof are indicated in FIG. 6 which is a histogram of obtained codon frequencies at two consecutive triplets. The expected value µ of each of the 10 codons in a sample of 62 is 6.2, if equal distribution is assumed. Looking at both triplets equally, all observed frequencies are well within a range of 2 standard deviations of a normal distribution. This result supports the hypothesis of an equal distribution since in this case more than 95% of the frequencies should be present within this range. The hypothesis is confirmed by the outcome that 13 of the 20 frequencies (65%) lie within a range of 1 standard deviation of an equal distribution thereby again meeting the statistical requirements of an equal distribution.

EXAMPLE 3

Manufacture of a Nucleic Acid Library with a Single Variable Position with Defined Ratios An example for the generation of a library with a single variable position whereby the codons occur in defined ratios is described in more detail in the following. Insofar the instant example illustrates an embodiment of the method according to the first aspect of the instant invention. The variable position contains 10 different codons. The codon usage was adapted to *E. coli*.

1) First Ligation

In a first reaction (R1), 20-200 pmol of a Splinker molecule, i.e. a first at least partially double-stranded oligonucleotide, with a GCC overhang (in 5'→3' direction, corresponding to the first stretch of the target sequence) were provided in a reaction vessel in 25 to 200 µl reaction buffer. Then, 20-200 pmol of a mixture of 10 Anchor molecules, i.e. the first oligonucleotide library, were added. These Anchors all have the same single-stranded overhang (GGC; in 5'→3' direction) that is complementary to the overhang of the Splinker molecule but they differ in their adjacent variable part representing the codons for 10 different amino acids (see table 1). All Anchor molecules were present in equimolar amounts (each Anchor 10% of the total amount). After addition of 10 to 50 U T4-DNA-Ligase the molecules were ligated for 60 minutes at 25° C. providing a plurality of first ligation products.

In a parallel reaction (R2), again 20-200 pmol of a Splinker molecule, i.e. a first at least partially double-stranded oligonucleotide, with a GCC overhang (in 5'→3' direction, corresponding to the first stretch of the target sequence) were provided in a reaction vessel in 25 to 200 µl reaction buffer. Then, 20-200 pmol of a mixture of 10 Anchor molecules, i.e. the first oligonucleotide library, were added. These Anchors also all have the same single-stranded overhang (GGC; in 5'→3' direction) that is complementary to the overhang of the Splinker molecule but they differ in their adjacent variable part representing the codons for 10 different amino acids (see table 1). In contrast to the first reaction this time one of the Anchor molecules (leading to a TTT overhang after restriction with Eam1104I, 30% of total amount) is present in excess to the other nine Anchors (7, 8% of total amount each). After addition of 10 to 50 U T4-DNA-Ligase the molecules were ligated for 60 minutes at 25° C. providing a plurality of first ligation products.

2) Isolation of a Plurality of First Elongated at Least Partially Double-Stranded Oligonucleotides The plurality of first ligation products was immobilized via its biotin moiety to a streptavidin-coated vessel or well for 15 minutes at room temperature. Unbound material was removed by washing three times with wash buffer (33 mM Tris/Acetate, 10 mM Magnesium Acetate, 66 mM, Potassium Acetate, pH 7.9). Then, 10 to 100 U of a restriction enzyme such as Eam1104I which is the second type IIS restriction enzyme were added in 25 to 200 μl reaction buffer followed by an incubation of 15 to 90 minutes at 37° C. The plurality of first elongated at least partially double-stranded oligonucleotides thus released was transferred to a new vessel or well.

This reaction was run in parallel for both R1 and R2.

3) Second Ligation 20-200 pmol of a mixture of 10 Anchor molecules, i.e. the second oligonucleotide library, were added to the first reaction (R1) containing the plurality of first elongated at least partially double-stranded oligonucleotides in 25 to 200 μl reaction buffer. The Anchor molecules differ in their single-stranded overhangs (corresponding to the second stretch of the target sequence) that are complementary to the overhangs provided by the plurality of first elongated oligonucleotides but are all identical in their adjacent part. All Anchor molecules were present in equimolar amounts (each Anchor 10% of the total amount). After addition of 10 to 50 U T4-DNA-Ligase the molecules were ligated for 60 minutes at 25° C. providing a plurality of second ligation products.

In parallel, 20-200 pmol of a mixture of 10 Anchor molecules, i.e. the second oligonucleotide library, were added to the second reaction (R2) containing the plurality of first elongated at least partially double-stranded oligonucleotides in 25 to 200 μl reaction buffer. The Anchor molecules differ in their single-stranded overhangs (corresponding to the second stretch of the target sequence) that are complementary to the overhangs provided by the plurality of first elongated oligonucleotides but are all identical in their adjacent part. One of the Anchor molecules contained an overhang (AAA) that is complementary to the overhang provided by the member of the plurality of the first elongated oligonucleotides that was present in an amount of 30% of the total amount in the first ligation and this Anchor was also present in an amount of 30% of the second oligonucleotide library. The other nine Anchors were present in an amount of 7.8% each. After addition of 10 to 50 U T4-DNA-Ligase the molecules were ligated for 60 minutes at 25° C. providing a plurality of second ligation products.

4) Isolation of a Plurality of Second Elongated at Least Partially Double-Stranded Oligonucleotides The plurality of second ligation products was immobilized via its biotin moiety to a streptavidin-coated vessel or well for 15 minutes at room temperature. Unbound material was removed by washing three times with wash buffer. Then, 10 to 100 U of a restriction enzyme such as Eam1104I which is the second type IIS restriction enzyme were added in 25 to 200 μl reaction buffer followed by an incubation of 15 to 90 minutes at 37° C. The plurality of second elongated at least partially double-stranded oligonucleotides thus released was transferred to a new vessel or well.

The reaction was run in parallel for both R1 and R2.

5) Third Ligation 20-200 pmol of an Anchor molecule with an overhang that is complementary to the overhang provided by the plurality of second elongated at least partially double-stranded oligonucleotides and which is the fourth at least partially double-stranded oligonucleotide was added to the plurality of second elongated at least partially double-stranded oligonucleotides in 25 to 200 μl reaction buffer. After addition of 10 to 50 U T4-DNA-Ligase the molecules were ligated for 60 minutes at 25° C. providing a plurality of third ligation products.

The reaction was run in parallel for both R1 and R2.

6) Synthesis of an Elongation Block

This elongation cycle comprising binding of the ligation products to the streptavidin surface, cleaving of the immobilized products by Eam1104I and ligation of the thus released elongated oligonucleotides with an appropriate Anchor was repeated three times resulting in a plurality of sixth ligation products, also referred to as elongation blocks. The conditions of each reaction steps were as described above.

The reactions were run in parallel for both R1 and R2.

7) Synthesis of the Final Product

The elongation blocks thus synthesized were used in the subsequent synthesis of the complete gene products, i.e. the nucleic acid library to be prepared, via the transposition method described earlier (international patent application WO 00/75368)

8) Quality Assessment of the Final Product

The final products, i.e. nucleic acid libraries having a single variable position, whereby 10 different codons can occur in equimolar (R1) or non-equimolar or biased (R2) ratios, were cloned into a standard vector and 96 single clones were sequenced each. As preferably used herein, the term biased refers to a mixture comprising various types of molecules, whereby one or several of the types of molecules are contained in a non-equimolar ratio compared to one or several others of said various types of molecules. The sequences appeared to be identical except from their particular variable position. The obtained distribution of the 10 different codons at the variable position is shown in Table 3.

TABLE 3

| Triplets | R 1 | R 2 |
|---|---|---|
| AAA | 12 | 30 |
| ATG | 4 | 5 |
| ACT | 7 | 9 |
| CCC | 9 | 6 |
| CCG | 11 | 10 |
| CTG | 14 | 6 |
| GAT | 9 | 8 |
| GCA | 8 | 7 |
| TTA | 15 | 4 |
| TGG | 7 | 11 |
| Total | 96 | 96 |

The respective figures together with the statistical analysis thereof are indicated in FIGS. 7 and 8 which are histograms of obtained codon frequencies at a single variable position. FIG. 7 shows the occurrence of the different codons within the library having the equimolar distribution (R1), FIG. 8 shows the occurrence of the different codons within the library where the AAA triplet is present in three-fold excess to the other codons (R2).

In R1, the expected value μ of each of the 10 codons in a sample of 96 is 9.6, if equal distribution is assumed. In this case it is expected that more than 95% of all codons lie within a range of two standard deviations ($\mu+/-2\sigma$). In this example, all observed frequencies are within a range of 2 standard deviations of a normal distribution, supporting the hypothesis of an equal distribution of codon frequencies. The hypothesis is confirmed by the outcome that 7 of the 10 frequencies (70%) lie within a range of 1 standard deviation of an equal distribution thereby again meeting the statistical requirements of an equal distribution (more than 65% frequencies within a range of 1 standard deviation).

In R2, the expected value μ for the AAA codon in a sample of 96 is 28.8, if it is assumed that the observed distribution follows the applied specifications. Correspondingly, the expected value for the other nine codons is 7.5. In case of a specified distribution it is expected that more than 95% of all codons lie within a range of two standard deviations ($\mu+/-$ 2σ). In this example, all observed frequencies are within a range of 2 standard deviations away from the respective expected value, supporting the hypothesis of the occurrence of the specified distribution of codon frequencies. The hypothesis is confirmed by the outcome that 8 of the 10 frequencies (80%) lie within a range of 1 standard deviation of the specified distribution thereby again meeting the statistical requirements of a specified distribution (more than 65% frequencies within a range of 1 standard deviation).

The features of the present invention disclosed in the specification, the sequence listing, the claims and/or the drawings may both separately and in any combination thereof be material for realizing the invention in various forms thereof.

The invention claimed is:

1. A method for preparing a nucleic acid library comprising a plurality of elements, whereby each element of said nucleic acid library comprises a first stretch of nucleotides, a second stretch of nucleotides and a third stretch of nucleotides, whereby the sequence of the first stretch of nucleotides and of the third stretch of nucleotides are identical in each element of the nucleic acid library and the elements of the nucleic acid library differ in the sequence of the second stretch of nucleotides, the method comprising the following steps:

a) providing a first at least partially double-stranded oligonucleotide comprising aa) a single-stranded overhang, whereby the single-stranded overhang provides for a nucleotide sequence corresponding to the sequence of the first or third stretch of nucleotides of the elements of the nucleic acid library; and ab) a recognition site, or part thereof, for a first type IIS restriction enzyme which cuts outside its recognition site;

b) providing a first oligonucleotide library comprising a plurality of members, whereby each member is a second at least partially double-stranded oligonucleotide comprising ba) a recognition site, or part thereof, for a second type IIS restriction enzyme which cuts outside its recognition site;

bb) a single-stranded overhang, whereby the single-stranded overhang is the same for each of the members of the first oligonucleotide library and is complementary to the single-stranded overhang of the first at least partially double-stranded oligonucleotide; and bc) whereby the members of the first oligonucleotide library differ in the sequence of a stretch of nucleotides and the sequence of said stretch of nucleotides corresponds to the sequence, or part thereof, of the second stretch of nucleotides of the elements of the nucleic acid library, wherein one or more nucleotide positions within the stretch of nucleotides differs at a controlled frequency;

c) ligating the first at least partially double-stranded oligonucleotide with the members of the first oligonucleotide library via their single-stranded overhangs, whereupon first ligation products are formed;

d) cutting the first ligation products with said second type IIS restriction enzyme in the nucleic acid sequence of the members of the first oligonucleotide library, and providing for a plurality of first elongated at least partially double-stranded oligonucleotides and for shortened second at least partially double-stranded oligonucleotides;

e) removing the shortened second at least partially double-stranded oligonucleotides;

f) providing a second oligonucleotide library comprising a plurality of members, whereby each member is a third at least partially double-stranded oligonucleotide comprising fa) a recognition site, or part thereof, for a third type IIS restriction enzyme which cuts outside its recognition site;

fb) a single-stranded overhang, whereby the single-stranded overhang is different for the members of the second oligonucleotide library and whereby such single-stranded overhangs of the third oligonucleotide are complementary to the single-stranded overhangs of the first elongated at least partially double-stranded oligonucleotides; and fc) a stretch of nucleotides which is identical in all members and corresponds to the sequence, or part thereof, of the third or first stretch of nucleotides of the elements of the nucleic acid library;

g) ligating the plurality of first elongated at least partially double-stranded oligonucleotides with the members of the second oligonucleotide library, whereby the single-stranded overhang of the first elongated at least partially double-stranded oligonucleotide is complementary to the overhang of the third at least partially double-stranded oligonucleotides, whereupon second ligation products are formed;

h) cutting the second ligation products with the third type IIS restriction enzyme in the nucleic acid sequence of the third at least partially double-stranded oligonucleotides, and providing for a plurality of second elongated at least partially double-stranded oligonucleotides and shortened third at least partially double-stranded oligonucleotides;

i) removing the shortened third at least partially double-stranded oligonucleotides;

j) providing fourth at least partially double-stranded oligonucleotides comprising ja) a single-stranded overhang, whereby the single-stranded overhang provides for a nucleotide sequence complementary to the single-stranded overhang of the second elongated at least partially double-stranded oligonucleotide; and jb) a recognition site, or part thereof, for a fourth type IIS restriction enzyme which cuts outside its recognition site;

k) ligating the fourth oligonucleotides and the plurality of the second elongated at least partially double-stranded oligonucleotides to form third ligation products;

l) cutting the third ligation products with the fourth type IIS restriction enzyme in the nucleic acid sequence of the fourth at least partially double-stranded oligonucleotides, and providing for a plurality of third elongated at least partially double-stranded oligonucleotides and shortened fourth at least partially double-stranded oligonucleotides; and m) removing the shortened fourth at least partially double-stranded oligonucleotides; and n) obtaining the nucleic acid library
wherein the nucleic acid library is a library of nucleic acid molecules coding for a peptide, polypeptide, protein, or functional nucleic acid;
wherein the peptide, polypeptide, or protein comprises one or several constant regions, and one or several variable regions;
wherein the one or several of the variable regions is/are encoded by the sequence of the second stretch of nucleotides of the elements of the nucleic acid library; and
wherein the second stretch of nucleotides of the elements of the nucleic acid library is the only difference between said elements.

2. The method according to claim 1, further comprising:
n) repeating steps j) to m), whereby the fourth at least partially double-stranded oligonucleotides of step j) are a further at least partially double-stranded oligonucleotide, the third ligation product in step k) is a further ligation product, the plurality of third elongated at least partially double-stranded oligonucleotides in step l) is a plurality of further elongated at least partially double-stranded oligonucleotides, and the shortened fourth at least partially double-stranded oligonucleotides of step l) are shortened further at least partially double-stranded oligonucleotides.

3. The method according to claim 2, whereby after ligation step k) the further ligation product is cleaved in the nucleic acid sequence of the further elongated at least partially double-stranded oligonucleotides.

4. The method according to claim 1, wherein the first type IIS restriction enzyme is selected from the group consisting of BpiI, BbsI, Esp3I, BsmBI, Eco31I, BsaI, BfuAI, FokI, BseRI, BbvI and BsgI.

5. The method according to claim 1, wherein the second, third, fourth, fifth and any further type IIS restriction enzyme is each and individually selected from the group consisting of EarI, Eam1104I, SapI, LguI, Ksp632I and BspQI.

6. The method according to claim 1, wherein the nucleic acid is a single-stranded nucleic acid and the length of the second stretch of nucleotides of the elements of the nucleic acid library consists of two nucleotides, three nucleotides, four nucleotides, five nucleotides, six nucleotides, seven nucleotides, eight nucleotides or multiples of three nucleotides.

7. The method according to claim 1, wherein the nucleic acid is a double-stranded nucleic acid and the length of the second stretch of nucleotides of the elements of the nucleic acid library consists of two nucleotides, three nucleotides, four nucleotides, five nucleotides, six nucleotides, seven nucleotides, eight nucleotides or multiples of three nucleotides.

8. The method according to claim 1, wherein the second stretch of nucleotides of the elements of the nucleic acid library is coding for one or several amino acids.

9. The method according to claim 1, wherein the second at least partially double-stranded oligonucleotides, the third at least partially double-stranded oligonucleotides, the fourth at least partially double-stranded oligonucleotides, the fifth and the further at least partially double-stranded oligonucleotides comprise a modification, whereby such modification allows for the immobilization of the oligonucleotides to a surface.

10. The method according to claim 9, whereby the modification is selected from the group consisting of a biotin residue, a digoxigenin residue, a fluorescein isothiocyanate residue, an amino compound and a succinyl ester.

11. The method according to claim 1, wherein the nucleic acid is selected from the group comprising aptamers, promoters, ribozymes, and RNAimediating molecules.

12. The method according to claim 1, wherein the peptide, polypeptide and protein is selected from the group consisting of peptide aptamers, enzymes, restriction enzymes, DNA binding domains, vaccines, antibodies, pharmaceutically active proteins, anticalines, DARPins, nanobodies, and AdNectines.

13. The method according to claim 1, wherein the controlled frequency comprises an equimolar distribution.

14. The method according to claim 1, wherein the controlled frequency comprises a non-equimolar or biased distribution.

15. A method for preparing a nucleic acid library comprising a plurality of elements, whereby each element of said nucleic acid library comprises a first stretch of nucleotides, a second stretch of nucleotides and a third stretch of nucleotides, whereby the sequence of the first stretch of nucleotides and of the third stretch of nucleotides are identical in each element of the nucleic acid library and the elements of the nucleic acid library differ in the sequence of the second stretch of nucleotides, the method comprising the following steps:
- a) providing a first at least partially double-stranded oligonucleotide comprising
  - aa) a single-stranded overhang, whereby the single-stranded overhang provides for a nucleotide sequence corresponding to the sequence of the first or third stretch of nucleotides of the elements of the nucleic acid library; and
  - ab) a recognition site, or part thereof, for a first type IIS restriction enzyme which cuts outside its recognition site
- b) providing a first oligonucleotide library comprising a plurality of members, whereby each member is a second at least partially double-stranded oligonucleotide comprising
  - ba) a recognition site, or part thereof, for a second type IIS restriction enzyme which cuts outside its recognition site, and a single-stranded overhang, whereby the single-stranded overhang is the same for each of the members of the first oligonucleotide library and is complementary to the single-stranded overhang of the first at least partially double-stranded oligonucleotide; and
  - bb) a stretch of nucleotides whereby the members of the first oligonucleotide library differ in the sequence of said stretch of nucleotides and the sequence of the said stretch of nucleotides of the members of the first oligonucleotide library corresponds to the sequence, or part thereof, of the second stretch of nucleotides of the elements of the nucleic acid library, wherein one or more nucleotide positions within the stretch of nucleotides differs at a controlled frequency;
- c) ligating the first at least partially double-stranded oligonucleotide with the first oligonucleotide library via their single-stranded overhangs, whereupon first ligation products are formed;
- d) cutting the first ligation products with said second type IIS restriction enzyme in the nucleic acid sequence of the member of the first oligonucleotide library, and providing for a plurality of first elongated at least partially double-stranded oligonucleotides and for shortened second at least partially double-stranded oligonucleotides, whereby such plurality of first elongated at least partially double-stranded oligonucleotides consist of various molecule species which differ in the sequence of the single-stranded overhang;
- e) removing the shortened second at least partially double-stranded oligonucleotides;
- f) providing a second oligonucleotide library comprising several subgroups of oligonucleotides and each subgroup comprising several members, whereby each member is a third at least partially double-stranded oligonucleotide comprising
  - fa) a recognition site, or part thereof, for a third type IIS restriction enzyme which cuts outside its recognition site;
  - fb) a single-stranded overhang, whereby the single-stranded overhang is different for the various subgroups of oligonucleotides of the second oligonucleotide library and whereby the single-stranded overhang of each one subgroup of the second oligonucleotide library is complementary to the single-stranded overhang of each of the first elongated at least partially double-stranded oligonucleotides; and
  - fc) a stretch of nucleotides which is different in the members of each subgroup of the second oligonucleotide library and corresponds to the sequence, or part thereof, of the second stretch of nucleotides of the elements of the nucleic acid library;
- g) ligating the plurality of the first elongated at least partially double-stranded oligonucleotides with the members of the second oligonucleotide library, whereby those molecules are ligated at the overhangs of which are complementary to each other, whereupon second ligation products are formed;
- h) cutting the second ligation products with the third type II S restriction enzyme in the nucleic acid sequence of the third at least partially double-stranded oligonucleotide, and providing for a plurality of second elongated at least partially double-stranded oligonucleotides and shortened third at least partially double-stranded oligonucleotides, whereby such plurality of second elongated at least partially double-stranded oligonucleotides consists of various subgroups which differ in their single-stranded overhangs;
- i) removing the shortened third at least partially double-stranded oligonucleotides;
- j) providing a third oligonucleotide library comprising several members, whereby each member is a fourth at least partially double-stranded oligonucleotide comprising
  - ja) a single-stranded overhang, whereby the single-stranded overhang provides for a nucleotide sequence complementary to the single-stranded overhangs of the second elongated at least partially double-stranded oligonucleotides; and jb) a stretch, preferably adjacent to said overhang which is identical in the various members and provides for the third or first stretch of nucleotides of the elements of the nucleic acid library, whereby the members of the third oligonucleotide library differ in their single-stranded overhangs and the overhangs correspond to the second stretch, or part thereof, of the nucleic acid library; and jc) a recognition site, or part thereof, for a fourth type IIS restriction enzyme which cuts outside its recognition site;

k) combining the plurality of second elongated at least partially double-stranded oligonucleotides and the third oligonucleotide library and ligating each molecule of the members of the third oligonucleotide library with one molecule of the plurality of the second elongated at least partially double-stranded oligonucleotides, whereby those molecules are ligated and the overhangs of which are complementary to each other, whereupon third ligation products are formed;

l) cutting the third ligation product with the fourth type IIS restriction enzyme in the nucleic acid sequence of the member of the third oligonucleotide library, providing for a plurality of third elongated at least partially double-stranded oligonucleotides and shortened fourth at least partially double-stranded oligonucleotides;

m) optionally removing the shortened fourth at least partially double-stranded oligonucleotides;

n) providing a fifth at least partially double-stranded oligonucleotide which has a single-stranded overhang, whereby the single-stranded overhang provides for a nucleotide sequence complementary to the single-stranded overhang of the plurality of third elongated at least partially double-stranded oligonucleotides, whereby the fifth oligonucleotide comprises a recognition site, or part thereof, for a fifth type IIS restriction enzyme which cuts outside its recognition site;

o) combining the plurality of third elongated at least partially double-stranded oligonucleotides and the fourth oligonucleotide library and ligating each molecule of the plurality of the third elongated at least partially double-stranded oligonucleotides with one molecule of the fifth at least double-stranded oligonucleotide, whereupon a fourth ligation product is formed;

p) cutting the fourth ligation product with the fifth type IIS restriction enzyme in the nucleic acid sequence of the fifth at least partially double-stranded oligonucleotide, providing for a plurality of fourth elongated at least partially double-stranded oligonucleotides and the shortened fifth at least partially double-stranded oligonucleotides;

q) optionally removing the shortened fifth at least partially double-stranded oligonucleotides;

r) obtaining the nucleic acid library, wherein the nucleic acid library is a library of nucleic acid molecules coding for a peptide, polypeptide, or protein;

whereby the peptide, polypeptide, or protein comprises one or several constant regions, and one or several variable regions;

wherein the one or several of the variable regions is/are encoded by the sequence of the second stretch of nucleotides of the elements of the nucleic acid library; and wherein the second stretch of nucleotides of the elements of the nucleic acid library is the only difference between said elements.

16. The method according to claim 15, further comprising the steps of:

r) repeating steps n) to q), whereby the fifth at least partially double-stranded oligonucleotide of step n) is a further at least double-stranded oligonucleotide, the fourth ligation product in step o) is a further ligation product, the plurality of fourth elongated at least partially double-stranded oligonucleotides in step p) is a plurality of further elongated at least partially double-stranded oligonucleotides, and the shortened fifth at least partially double-stranded oligonucleotide of step p) is a shortened further at least partially double-stranded oligonucleotide.

17. The method according to claim 16, whereby after ligation step o) the further ligation product is cleaved in the nucleic acid sequence of the further elongated at least partially double-stranded oligonucleotide.

18. A method for the manufacture of a nucleic acid molecule library comprising a plurality of elements, whereby the elements comprise at least one constant stretch and at least one variable stretch and whereby the at least one constant stretch comprises a nucleotide sequence which is the same in all of the elements, and the at least one variable stretch comprises a nucleotide sequence which is different in all of the elements, the method comprises the following steps:

a) providing a first oligonucleotide, whereby the first oligonucleotide is either an at least partially double-stranded oligonucleotide having a single-stranded overhang and comprising a recognition site for a first type IIS restriction enzyme which cuts outside its recognition sequence, or a nucleic acid library comprising a plurality of elements, whereby the nucleic acid library is the nucleic acid library according to claim 1 or 4 and the elements of the nucleic acid library have a single-stranded overhang, and the elements of the nucleic acid library comprise a recognition site for a first type IIS restriction enzyme which cuts outside its recognition sequence;

b) providing a second oligonucleotide, whereby such second oligonucleotide is a nucleic acid library comprising a plurality of elements, whereby the nucleic acid library is the nucleic acid library according to claim 1 or 4 and the elements of the nucleic acid library have a single-stranded overhang which is complementary to the single-stranded overhang of the oligonucleotide provided in step a), the elements of the nucleic acid library comprise a recognition site for a second type IIS restriction enzyme which cuts outside its recognition sequence, whereby the second type IIS restriction enzyme of the elements of the nucleic acid library is different from the first type IIS restriction enzyme of the oligonucleotide provided in step a);

c) combining the oligonucleotides of step a) and step b) and ligating one molecule of the oligonucleotide of step a) with each one molecule of each one element of the nucleic acid library of step b) via their single-stranded overhangs under the proviso that the oligonucleotide of step a) is different from the nucleic acid library according to claim 1 or 4;

or combining the oligonucleotides of step a) and step b) and ligating each one molecule of each one element of the nucleic acid library of step a) with each one molecule of each one element of the nucleic acid library of step b) via their single-stranded overhangs under the proviso that the oligonucleotide of step a) is a nucleic acid library according to claim 1 or 4;
d) optionally removing non-reacted reactants and enzymes;
e) cleaving the ligation product of step c) with a type IIS restriction enzyme which cuts outside its recognition sequence, whereby the cleavage occurs in the oligonucleotide of step a) or step b) providing for a library of extended nucleic acid molecules; and
f) optionally separating the extended nucleic acid molecules from the reaction mixture;
g) obtaining the nucleic acid library.

19. The method according to claim 18, whereby the step a) to f) are repeated under the provisos that the oligonucleotide of step a) is a third oligonucleotide which is the library of extended nucleic acid molecules provided in step e), and the oligonucleotide of step b) are fourth oligonucleotides which are either a library according to claim 1 or 4, or fourth at least partially double-stranded oligonucleotides having a single-stranded overhang and comprising a recognition site for a fourth type IIS restriction enzyme which cuts outside its recognition sequence, whereby the third and the fourth oligonucleotides each comprise a single-stranded overhang and whereby both overhangs are complementary to each other; when combining the oligonucleotides of step a) and step b) and ligating one molecule of each one element of the nucleic acid library of step a) with one molecule of the oligonucleotide or each one molecule of each one element of the nucleic acid library of step b) via their single-stranded overhangs, the oligonucleotide of step a) is different from the oligonucleotide or library of extended nucleic acid molecules of step b); or when combining the oligonucleotides of step a) and step b) and ligating each one molecule of each one element of the nucleic acid library of step a) with one molecule of the oligonucleotide or each one molecule of each one element of the nucleic acid library of step b) via their single-stranded overhangs, the oligonucleotide of step a) is a library of extended nucleic acid molecules; and wherein in step e) a further library of extended nucleic acid molecules is obtained.

20. The method according to claim 18, wherein the variable stretch is provided by the second stretch of the elements of the nucleic acid library as described in claim 1.

21. The method according to claim 18, wherein the constant stretch or part thereof is provided by the first stretch and/or the third stretch of the elements of the nucleic acid library as described in claim 1.

\* \* \* \* \*